(12) United States Patent
Toledano

(10) Patent No.: US 6,338,737 B1
(45) Date of Patent: Jan. 15, 2002

(54) FLEXIBLE ANNULAR STAPLER FOR CLOSED SURGERY OF HOLLOW ORGANS

(76) Inventor: Haviv Toledano, 69 Keren Hayessod St., 27053 Kiryat Bialik (IL)

(*) Notice: Subject to any disclaimer, the term of this patent is extended or adjusted under 35 U.S.C. 154(b) by 0 days.

(21) Appl. No.: 09/846,362

(22) Filed: May 2, 2001

Related U.S. Application Data

(63) Continuation of application No. 09/214,039, filed on Dec. 28, 1998, now abandoned.

(30) Foreign Application Priority Data

Jul. 17, 1997 (WO) .............................. PCT/IB97/00887

(51) Int. Cl.⁷ .............................................. A61B 17/08
(52) U.S. Cl. ................... 606/219; 227/176.1; 227/175.1
(58) Field of Search ................... 606/219, 152, 606/153, 139; 227/175.1, 19, 176, 179.1, 178.1, 181.1, 180.1

(56) References Cited

U.S. PATENT DOCUMENTS

| 4,351,466 A | * | 9/1982 | Noiles .......................... 227/8 |
| 5,395,030 A | * | 3/1995 | Kuramoto et al. .......... 227/179 |
| 5,533,661 A | * | 7/1996 | Main et al. ............... 227/176.1 |
| 5,860,581 A | * | 1/1999 | Robertson et al. ....... 227/179.1 |

\* cited by examiner

Primary Examiner—Stephen P. Garbe
Assistant Examiner—Lien Ngo

(57) ABSTRACT

A greatly improved flexible annular stapler for joining tubular organs is disclosed. The novel stapler features greater accuracy of operation and better control by the operator, as well as additional functions, such as internal illumination and viewing facility, and accommodation of a large number of accessories, such as fibroscopes and catheters. The novel stapler, moreover, features easy attachability of both stapling jaws and easy detachability of the head. The novel features are particularly useful for closed surgery. Also disclosed are novel methods and procedures for using a flexible annular stapler and the novel features disclosed herein—particularly under conditions of closed surgery.

26 Claims, 18 Drawing Sheets

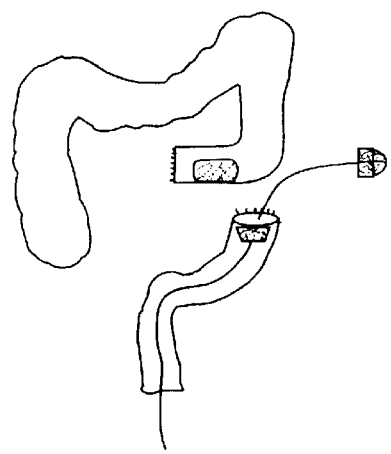
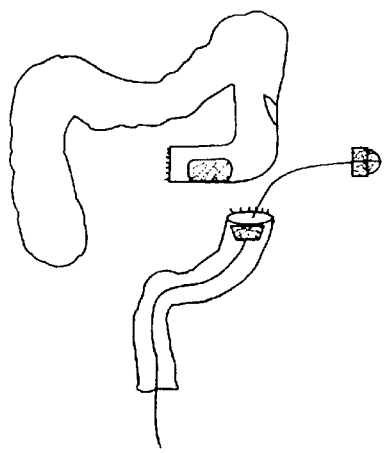
Fig. 12a · · · · · · · · · · Fig. 12b
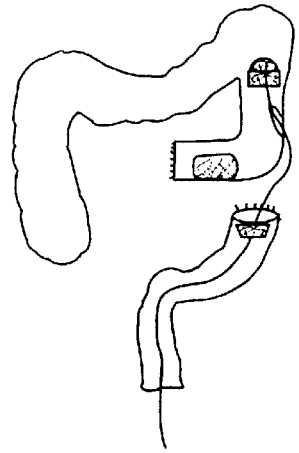
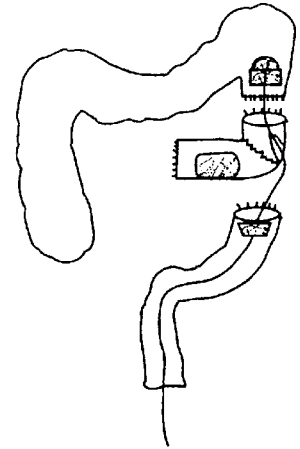
Fig. 12c · · · · · · · · · · Fig. 12d
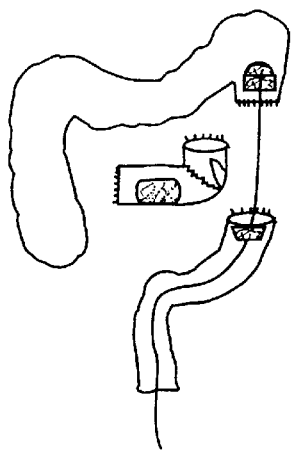
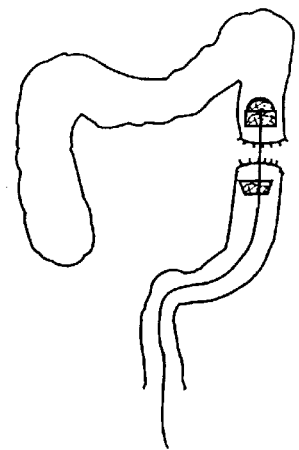
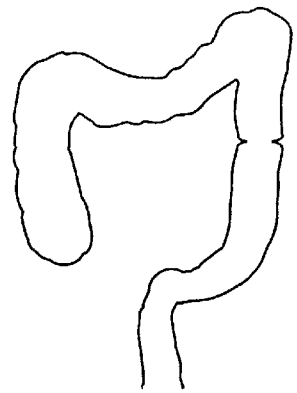
Fig. 12e · · · · Fig. 12f · · · · Fig. 12g

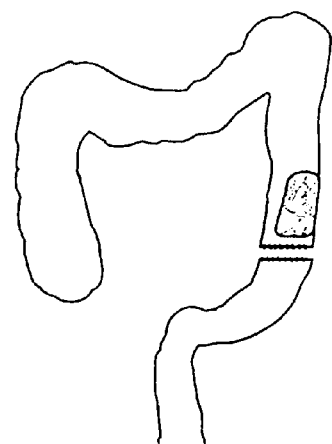
Fig. 13a
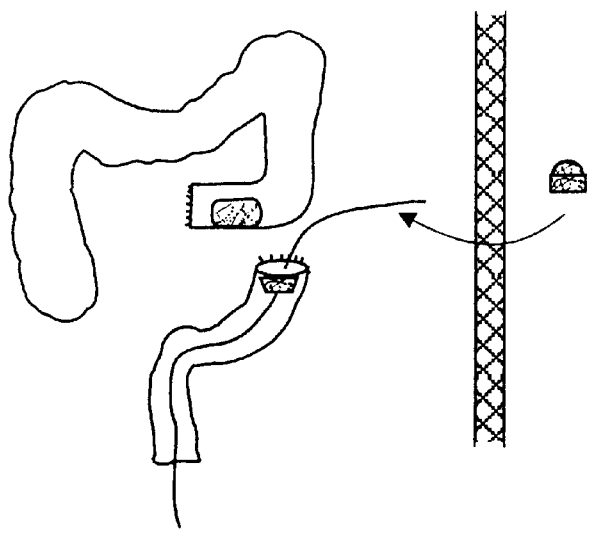
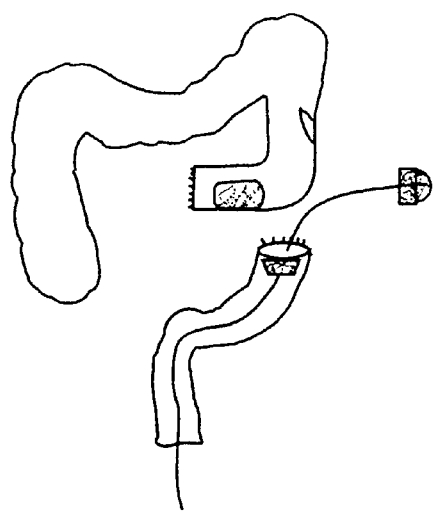
Fig. 13b
Fig. 13c

FLEXIBLE ANNULAR STAPLER FOR CLOSED SURGERY OF HOLLOW ORGANS

This is a Continuation Application of U.S. patent application Ser. No. 09/214,039, filed on Dec. 28, 1998, now abandoned.

FIELD AND BACKGROUND OF THE INVENTION

The present invention relates to excision of a section of a hollow or tubular soft organ, such as the digestive tube, and rejoining the remaining ends and, more particularly, to methods for performing these operations under conditions of closed surgery, using a flexible annular stapling and cutting instrument. The invention also relates to an improved construction of such an instrument.

Various ailments of the digestive tube, particularly of the esophagus, the stomach, the small intestines and the colon, such as tumors, chronic inflammation or other disorders, often require excision of a portion of the tube, followed by rejoining of the remaining end segments, through anastomosis, to reestablish continuity of the tube. In some cases it is necessary to thus join one organ to another; for example, the cut end of the small intestines may be joined to the colon, or the cut end of the duodenum may be joined to the stomach. In some other cases, two organs or two portions of the same organ may be joined side-to-side (rather than end-to-end or end-to-side, as in the above cases). In the discussion to follow and in the claims, the terms "parts of hollow organs" or just "parts" will be used, for brevity, to collectively denote the two parts to be joined, and the terms "part of a hollow organ" or just "apart"—to denote each of the two parts to be joined, whether they are truly two different hollow organs or two segments of the same hollow organ.

It has been common practice since the end of the '50s to use, for the purpose of the anastomosis, a suitable annular stapling and cutting instrument. An example of such an instrument, to be referred to herebelow as stapler, is depicted in FIG. 1A. The stapler basically consists of a tubular main body, at one end of which is an annular staple gun, while the other end serves as a handle and has a knob and activation levers thereon. A rod is slidably disposed inside the tubular body, protruding through the staple gun and terminating with a round head that contains an annular anvil. The staple gun contains a set of surgical stapling pins, arranged in one or two concentric circles and a circular knife inside these circles. On the face of the anvil are short grooves, one opposite each staple pin, with arc-like depth profile. During surgery, this stapler is used, for example, to rejoin end segments of the intestines after excision, by inserting it through a longitudinal cut in the side of the intestines and through the ends of both segments, then annularly folding and temporarily sewing one end over the face of the gun and one end over the anvil; the latter operation forms the ends into partially closed flange-like butts. Subsequently, by turning the knob, the head with the anvil is pulled toward the face of the gun, thus bringing the butts into mutual contact. Finally, by activating a lever on the handle, the staple pins are pushed through the flanges into the grooves in the anvil until they are bent tight; at the same time, the circular knife cuts away the inner disks of the two adjoining flanges, leaving an annular ring as the joint.

This, conventional, type of stapler has several shortcomings:

It always requires an extra, longitudinal, cut; for multiple excisions, multiple extra cuts are needed.

It is not suitable for hard-to-reach or complicated portions of the intestines, such as those inside the pelvis, nor for the duodenum; operation on the esophagus or the stomach is difficult.

It is suitable almost only for end-to-end joints.

The temporary sewing of the butt ends is difficult and the depth of the resulting flanges is small, thus risking leakage.

French patent FR 9204490 to the present applicant, which is incorporated into the present disclosure by reference, discloses a novel annular stapler that differs from the one described hereabove essentially in the following (see FIG. 1B for an external view and FIG. 1C for a longitudinal-sectional view): The main, tubular, body consists of a flexible hose 26, which can be of any length and to one end of which an anvil assembly 18 is attached. Through hose 26 is slidably disposed a flexible cable 21, one end of which is pointed and to which a head 11 is attachable. The other end of cable 21 is attached to a handle 30 by means of a long screw 52, engaged by a nut 51, which is connected to a knob 46 so that turning the knob causes the cable to slide along the hose and thus—the head to move with respect to the anvil. The head contains a cartridge with staple pins and a rigid hammer assembly 15 (to be refrred to as hammer) that includes fingers, to push the pins, and a circular knife. Hammer 15 is connectable to the end of cable 21 by a screw-like arrangement. Connected to the hammer through a spring is an annular base plate, which holds the cartridge of pins and has slots for passage of the pins. Cable 21, which may be hollow, has a flat outer surface, which matches a flat in the shape of a central hole in anvil 18 through which the cable slides; this is in order to keep the head angularly aligned with respect to the anvil prior to stapling. In handle 30 there is a window 54, through which a millimeter scale 42, attached to cable 21 is viewable, together with a fixed pointer. Operation of this stapler is similar to that of a conventional one, except that the stapling and cutting operation, after the two butts have made contact, is actuated automatically by continued turning of the knob (rather than activating a lever.

This novel stapler avoids the shortcomings of the conventional one, listed hereabove. In particular, it enables reaching any segment of the digestive tube—either through a natural opening (mouth or anus) or through a single, conveniently located cut. It also enables end-to-side or side-to-side joints.

Even so, the novel stapler of French patent FR 9204490 (to be referred to as the French patent) still has a few shortcomings and many as yet unrealized potentialities. One shortcoming is that in the disclosed construction there is an appreciable length of cable between the point at which the cable emerges from the anvil and the point at which it enters the head structure, even when these two components are at their closest approach. This may allow some twist in the cable and consequently some angular misalignment between the staple pins in the head and the grooves in the face of the anvil, which may cause malfunctioning of the stapling action. Likewise, because of uneven back pull of an intestinal butt, the faces of the two components may not be parallel, or may not be axially aligned prior to the stapling action, which, again, could cause malfunction. Another shortcoming of the instrument is in the operation of the handle; turning the knob may not be the optimal way to activate the stapling and cutting operation. Yet another shortcoming is the difficulty with which the head or anvil are attachable or detachable, making such operations within the body, as would be advantageous in certain procedures, close to impossible.

The unrealized potentialities are mainly associated with a new possible mode of its employment, a mode that was not contemplated in the French patent but is the subject of the present invention, namely closed surgery. The practice and techniques of closed surgery, such as laparoscopy and thoracoscopy, have made tremendous progress over the past five years and many surgical procedures on internal organs are now carried out in this mode. whereas in conventional, open, surgery, a relatively large incision is made in the abdominal wall or chest, closed surgery is characterized by insertion of very thin tools through otherwise intact walls—usually with the aid of small tubular ports, called trocars, which also serve to seal the openings during operation. Some of these tools serve for viewing and usually include a video system so that the entire operation is viewed and monitored on a video screen. The main advantages of closed surgery are (a) the much reduced trauma resulting in fewer complications and much faster recuperation, which, in turn, shortens hospitalization and costs, (b) reduced risk of infection and (c) considerable reduction of scars.

Closed surgery of the digestive tube is also being practiced. However, because the only practical instrument now available for anastomosis is the rigid type described hereabove, which has to be operated under open conditions, the surgery ends up being, in part, of the open type (such as laparoscopically assisted surgery) and thus foregoes some of the advantages listed above. Basically, a flexible stapler, as described hereabove and contrary to a conventional, rigid, stapler, lends itself to completely closed surgery (such as laparospcopy and thoracoscopy), since the instrument is insertable either through the natural openings or through a suitable opening in the intact wall and can reach almost any location. However, such use of a flexible stapler has not yet been attempted nor, to the best of the inventor's knowledge, even been suggested. Moreover, there are certain aspects of this type of surgery that render direct utilization of the instrument, as disclosed in the French patent, difficult or impractical. For example, the preliminary circular sewing of the butt ends over the instrument's head or anvil, difficult even during open surgery, is close to impossible. Under certain circumstances it is preferable to place the active part of the instrument in the affected area prior to excision; it is then difficult to sense its position within the intestines. Also, there is a need for endoscopy during the operation and it may be difficult to insert or manipulate both the endoscope and the flexible stapler simultaneously in the same tube. A similar difficulty holds for internal ultrasonic examination.

Since, as stated, use of a flexible stapler in closed surgery has not yet been attempted and since, moreover, such an instrument is not yet available, there has been no clinical experience with anastomosis in the digestive tube under conditions of closed surgery and certainly no experience using such an instrument. Thus, no suitable procedures have so far been developed, which fact keeps the clinicians and patients from benefiting from the tremendous potential advantages of the technology and also hinders potential acceptance by clinicians of the instruments when they become available.

There is thus a recognized need for, and it would be highly advantageous to have, an improved stapler for anastomosis in the digestive tube that will overcome the shortcomings of presently known instruments and will, moreover, enable such operation under conditions of closed surgery. There is, furthermore, a need for practical methods and procedures for utilizing such an instrument under conditions of closed surgery.

SUMMARY OF THE INVENTION

The present invention successfully addresses the shortcomings of the presently known configurations by providing an improved and more practical flexible annular stapler, which is applicable to a wide variety of procedures and surgical conditions, including closed surgery.

More specifically, the stapler of the present invention enables accurate allignment of the head to the anvil during stapling, more convenient activation of the stapling operation itself, possibility of introducing into the stapler, or building into it, various auxiliary tools, such as imagers and catheters, and easy attachability and detachability of the head and of the anvil, all of which are particularly advantageous for operation under conditions of closed surgery.

The present invention discloses a novel construction of a flexible annular stapler with a large number of optional features and attachments. It also discloses novel methods and procedures for using a flexible stapler, in general, and the improved stapler of the present invention in particular, for anastomosis of hollow organs, which methods contribute to more efficient and cleaner operation.

According to the present invention there is provided a flexible annular surgical stapler for stapling together two parts of hollow organs, the stapler comprising (a) an elongated flexible tubular body;
(b) a handle attached to a first end of the body
(c) a first jaw having an axial hole therethrough and two faces, a first face being attached to the second end of the body;
(c) a flexible cable slidably disposed inside the body and through the hole, the cable consisting of two portions, a first portions defining an end segment, at least part of which protrudes from the second face of the first jaw; and
(d) a second jaw, defining a head, being attachable to the end segment; the hole in the first jaw having a non-circular cross-sectional shape and the end segment having a complementary cross-sectional shape such as to allow easy sliding of the end segment through the hole while keeping their mutual angular orientation about the axis of the hole fixed;

wherein one of the first and second jaws includes a hammer and the other of the first and second jaws includes an anvil.

According to further features in preferred embodiments of the invention described below, the end segment of the cable is stiffer than the rest of the cable and may be formed separately.

According to still further features in the described preferred embodiments, the handle includes (i) a housing attached to the second end of the body,
(ii) an elongated externally threaded member disposed inside the housing and attached to the second portion of the cable,
(iii) a turning assembly, which includes an internally threaded member that engages the externally threaded member, and a knob outside the housing, and
(iv) a lever assembly, which includes a manually pressable lever;

the turning assembly being operative, upon turning of the knob, to cause the cable to slide along the body; and the lever assembly being operative to keep the turning assembly at a fixed axial position relative to the housing, when the lever is not being pressed, and to pull the turning assembly axially away from the body, when the lever is being pressed.

According to other features of the invention, the head is attachable to the end segment, and the anvil is attachable to the body, by a snap coupling.

According to yet other features of the invention, the cable has, over its entire length, a passageway therethrough for insertion of one or more additional tools or parts thereof or to pass air or fluid to the end cap or to a balloon attached thereto.

According to another embodiment, the stapler further comprises an ultrasonic transducer for ultrasonically probing tissue near the head, or an illuminator for illuminating tissue near the head, or imaging optics for viewing tissue near the head, the imaging optics including a coherent fibers bundle disposed inside and along a passageway through the cable, or a video camera, for viewing tissue near the head.

Also according to the present invention there is provided a method for joining two parts of hollow organs over an annular area defined on a plane in each of the two parts, whereby each part has an opening through the respective plane essentially inside the respective annular area, the method sequentially comprising the steps of (a) providing a flexible annular stapler having two round jaws;

(b) inserting the jaws into a first one of the two parts and advancing the jaws to where one jaw is inside the first part and the other jaw is inside the second one of the two parts, each jaw being substantially near the respective plane;

(c) for each of the two parts, shrinking the opening so as to form an at least partially closed butt that encloses the respective one of the jaws; and (d) operating the annular stapler so as to pull the two the butts together and essentially combine the two annular areas into a combined annular area, to staple the two organs or segments to each other over the combined annular area and to cut away portions of the butts that are central to the combined annular area.

According to further features of the invention, steps (b) through (d) are carried out under conditions of closed surgery, inserting is effected through a natural opening of the patient's body and shrinking includes, with respect to each of the two parts, pressing the tissue surrounding the opening to form a pair of adjoining lips and stapling the lips together by means of a linear stapler An alternative method according to the invention, provides for joining two parts of hollow organs over an annular area defined on a plane in each of the two parts, under conditions of closed surgery performed on a patient, the method comprising the steps of (a) providing a flexible annular stapler having a flexible body, two round jaws and a flexible cable slidable through the body and through a first one of the jaws and having an end protrudable from the first jaw, the first one of the jaws being attachable to the body and the second one of the jaws being attachable to the end of the cable, both of the jaws being initially detached;

(b) inserting the flexible body through the patient's body wall;

(c) introducing the first jaw through the patient's body wall and attaching it to the flexible body;

(d) introducing the second jaw through the patient's body wall and attaching it to the end of the cable;

(e) having the first jaw inside the first one, and the second jaw inside the second one, of the two pairs of hollow organs and having each of the two parts form an at least partially closed butt at or near the respective plane, the butt enclosing the respective one of the jaws; and (f) operating the annular stapler so as to pull the two butts together, to staple the two organs or segments to each other over an annular area and to cut away portions of the butts that are central to the annular area.

BRIEF DESCRIPTION OF THE DRAWINGS

FIGS. 11 through 16 are sketches of a human colon, illustrating methods according to the present invention of employing a flexible annular stapler in surgical procedures.

DESCRIPTION OF THE PREFERRED EMBODIMENTS

The present invention is of methods and apparatus for performing anastomosis of the digestive tube under closed surgery conditions. Specifically, the present invention includes an improved flexible annular stapler and can be used to conveniently and quickly perform such anastomosis at any location and in conjunction with any of a large variety of surgical procedures, which may include end-to-end, end-to-side and side-to-side joints.

The principles and operation of an improved annular stapler, as well as new surgical methods utilizing it, according to the present invention may be better understood with reference to the drawings and the accompanying description.

Figure 2:
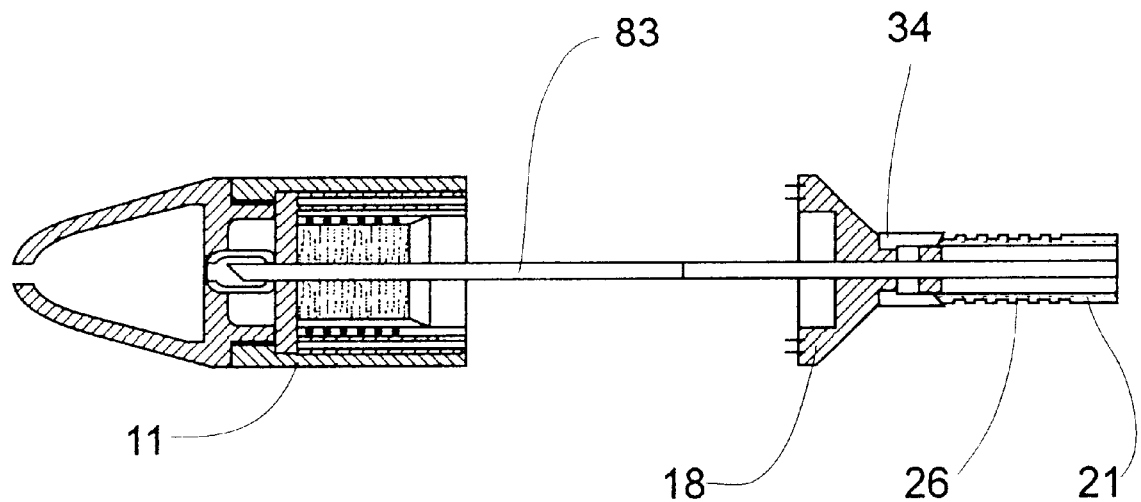
FIG. 2 is a longitudinal sectional view of the end portion of a stapler according to the present invention, showing the anvil, the head and the end segment of the flexible cable.

Referring now to the drawings, FIG. 2 illustrates the end portion of a flexible stapler similar to that of the French patent, but with an improved head-to-anvil alignment control. Flexible cable 21 is slidingly disposed inside flexible hose-like body 26 along its entire length. A segment 83 of the cable, a few centimeters long, at the end that is generally attachable to head 11 is designated as end segment. According to a preferred embodiment of the invention, end segment 83, which slides through hole 34 in anvil 18 when the head is relatively close to the anvil, is made to be substantially stiffer than the rest of the cable. According to an alternative preferred embodiment, the stiff end segment 83 is a separately produced component, to be called extension rod, which is attached to the end of cable 21.

According to the invention, there is also more freedom in choosing a suitable cross-sectional shape (rather than a circle with a flat, as specified in the French patent) for the end segment, the cable and the hole, namely one that will optimize the stiffness of the end segment (or extension rod), with respect to both bending and twisting, as well as its rotational fixation within the similarly shaped hole in the anvil (and thus—of the head with respect to the anvil). The relative cross-sectional sizes of end segment 83 and hole 34, and thus the fit between them, should preferably be closely controlled, so as to maximally fix their relative angular position, on the one hand, and allow easy sliding, on the other hand. Cable 21 itself preferably has an identical shape, though its fit within the hole need not be as tight. Clearly, during operation, as the head is pulled toward the anvil, the stiff end segment slides through the matching hole in the anvil; their cooperation ensures that the opposing faces of the head and the anvil become essentially parallel and mutually aligned, both laterally and rotationally, while approaching each other. Another advantage of a stiff end segment is that it lends itself better to forming a pointed end for piercing tissue, as is required in certain procedures. It is noted that the stiff end segment (or extension rod) may be hollow, just as the rest of the cable, to form a through passageway.

It is noted that the construction according to the French patent, which serves as the preferred basis for the present invention, calls for an anvil to be part of the mechanical assembly that is attached to the end of the tubular body, while the mechanical assembly that is attached, or attachable, to the end of the cable (or the extension rod), which is referred to as the head, contains, inter alia, a circular knife, a hammer and a cartridge of stapling pins. In the context of the present invention it is equally possible, and may sometimes be preferable, that the anvil be placed in the head and the hammer and stapling pins—in the assembly attached to the body. The knife, moreover, may be independently placed in either one of the two assemblies. Therefore, for the sake of both brevity and generality, the two assemblies will sometimes, when no differentiation is necessary be referred to as jaws. When differentiation is necessary, the jaw attached to the end of the body will be referred to as anvil and the jaw attached to the end of the cable will be refrred to as the head. The use of the term anvil is based on the examplary configuration for convenience only, with the other configuration (i.e., anvil in the head and hammer and pins in the jaw attached to the body) being understood to also come within the scope of the present invention. Sometimes the tenn anvil is used to denote the part itself (rather than the jaw), in which case the meaning will be understood from the context.

Figure 1A:
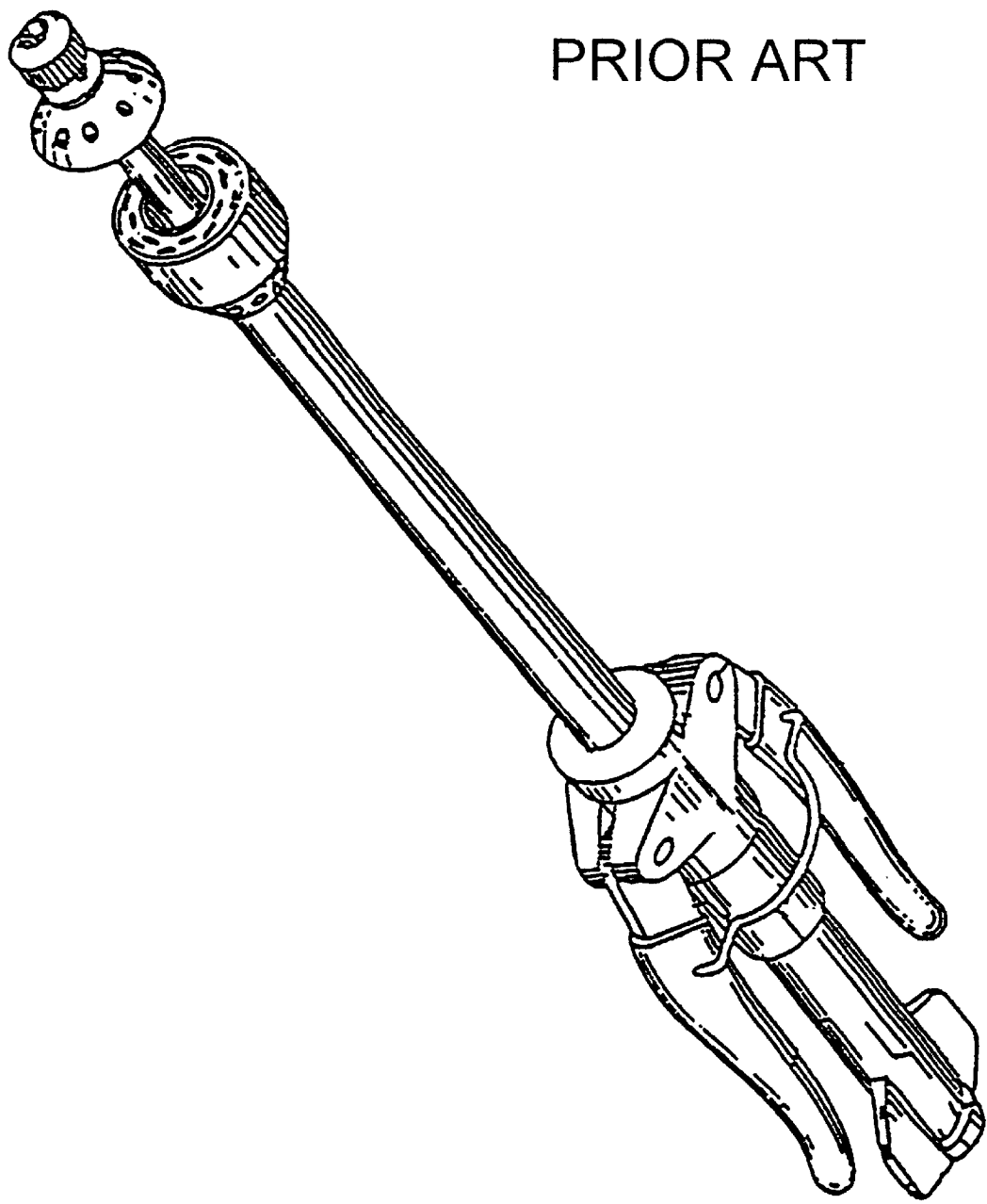
FIG. 1A is an isometric drawing of an annular stapler of prior art.
Figure 1B:
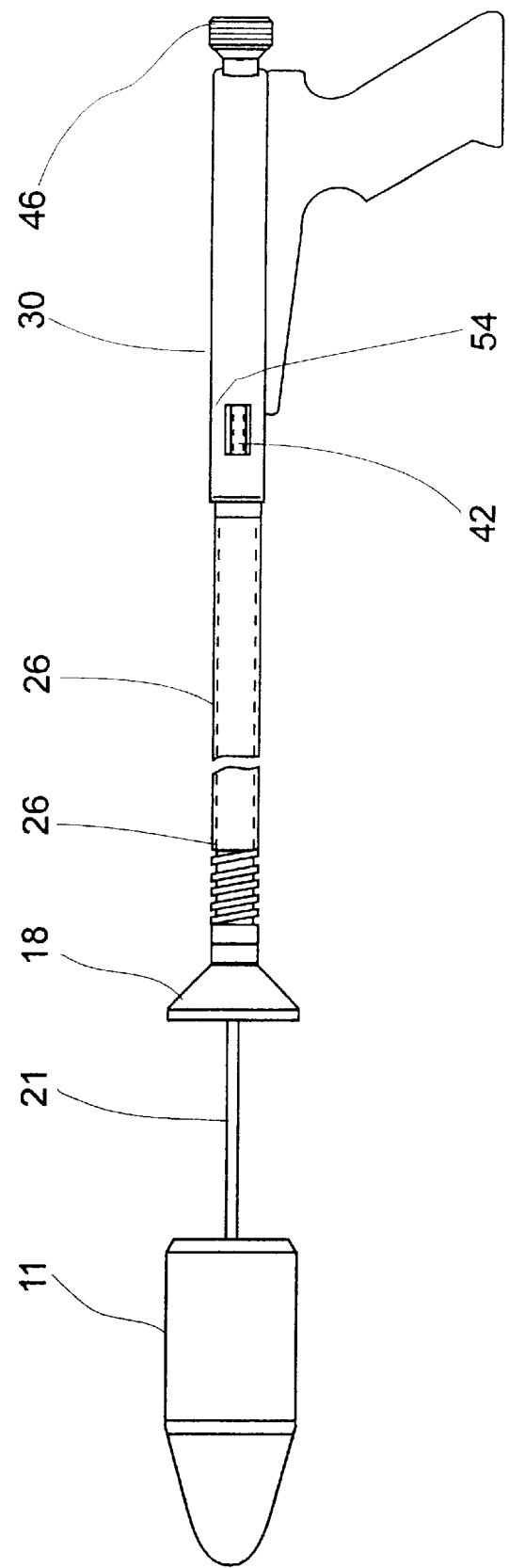
FIG. 1B is an external side view of a flexible annular stapler of prior art.
Figure 1C:
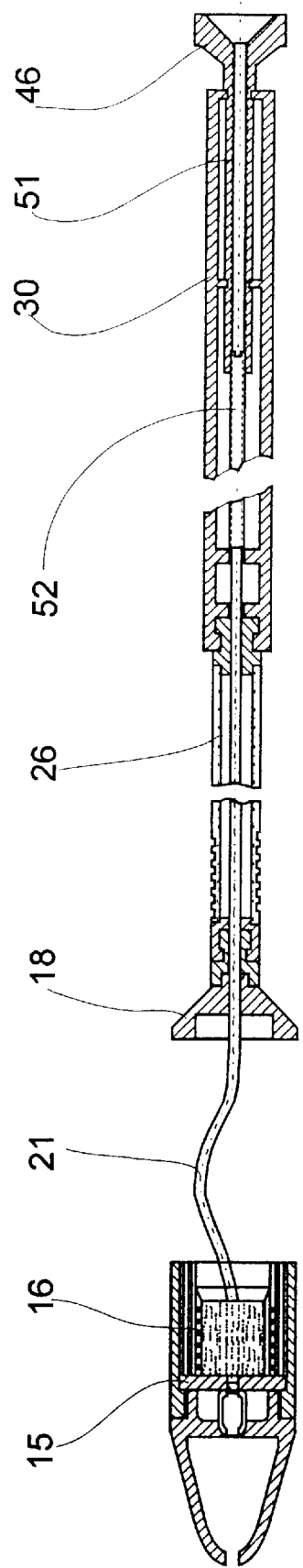
FIG. 1C is a longitudinal sectional view of the stapler of FIG. 1B.
Figure 3:
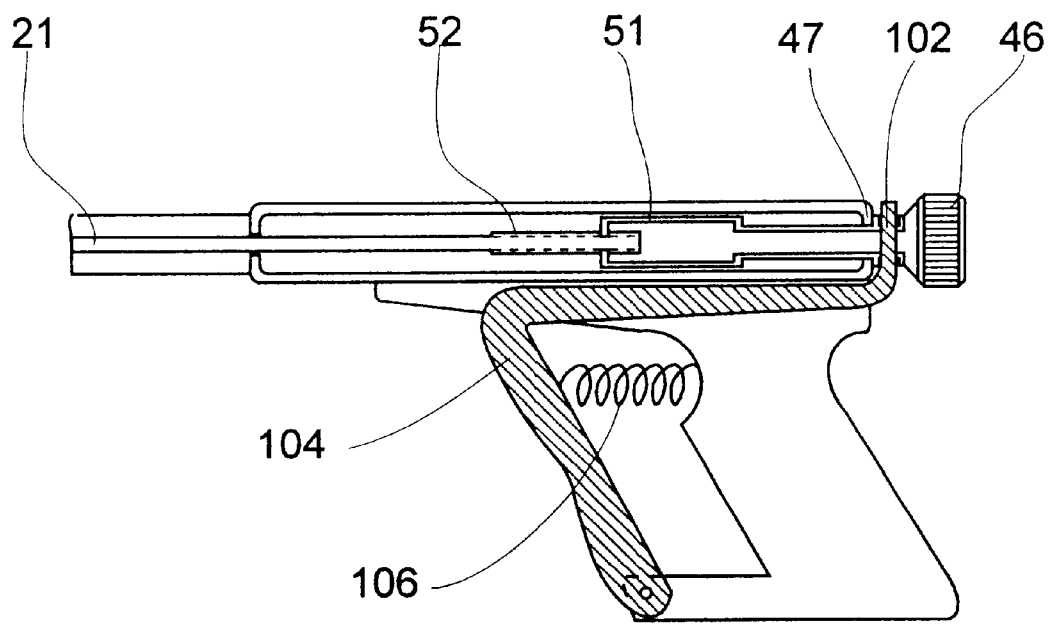
FIG. 3 is a longitudinal sectional view of the handle of a stapler according to one feature of the present invention.

FIG. 3 illustrates an improved handle portion of the flexible stapler according to the present invention. As before, the end of flexible cable 21 is connected to a long screw 52, which is engaged by a nut 51 that is rotationally activated by a manual knob 46. However, knob 46, rather than being axially held by an annular tongue-and-groove arrangement at the end of handle housing 47, is now held by a similar tongue-and-groove arrangement in a separate plate 102 that is attached to a lever 104, which is loaded by spring 106. Spring 106 acts to normally keep plate 102 adjacent to, and touching, end 47 of the handle housing; the axial movement of the cable inside the body is then controlled by turning knob 46, as before. When lever 104 is pressed, though, the knob is pushed away from the handle, pulling the entire cable assembly with it. This feature would normally be utilized as follows: At the beginning of operation the knob is turned counterclockwise until the head and anvil are the desired distance apart. After attaching the butt ends of the tubular organ being operated on to the jaws, the knob is turned clockwise, causing the two butts to approach each other. The surgeon watches millimeter scale 42 (FIG. 1B) attached to the cable and viewable, together with a fixed pointer, through window 54 in the handle. When the position of the scale indicates that the two butt ends have made contact, the surgeon pushes lever 104 and thus causes the cable to be pulled further and to thus activate the stapling and cutting mechanism. Alternatively, there may be a stopper attached to screw 52 at the end of the cable inside the handle, such that will impinge on the end of nut 51 when the two butts have made contact and thus prevent any further travel due to turning of the knob. The advantage of this feature is that it provides the surgeon with tactile sense, and thus better control, of the stapling operation.

Figure 4A:
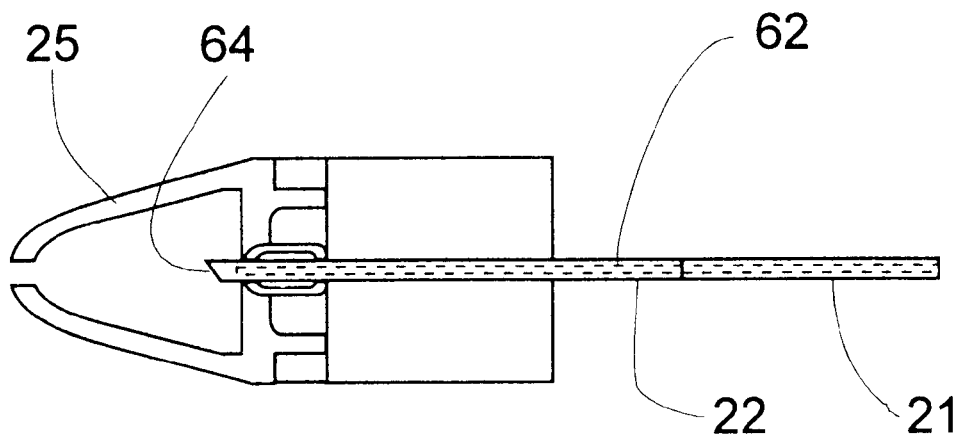
FIG. 4A is a longitudinal sectional view of the head and the cable's end segment of the stapler of the present invention, configured for illumination.

Referring now to FIG. 4A, which illustrates the head portion of a preferred embodiment of a flexible stapler with an internal illuminator, there is shown a stapler basically similar to the one disclosed in the French patent, the essential differences being as follows: There is a hollow passageway along the entire flexible cable 21 and its end segment 83. Through this passageway there is disposed an optical fiber 62, or a bundle of fibers. The end of this fiber that is in the handle (not shown) is optically coupled to a fiber illuminator; the fiber illuminator and the method of coupling it to the fiber may be any of a number known in the art. The fiber illuminator may be attached to the handle or it may be in a stationary console, with the fiber extending to it from the end of the handle. The other end of fiber 62, which protrudes from end segment 83 of the cable, is optically coupled to a diffuser 64, or a similar optical element, inside cap 25 of the head of the stapler. Cap 25, which forms the end of the head farthest from the cable and will therefore be referred to as the end cap, and which usually has a conical or hemispheric shape, is here made of an optically translucent or transparent material, such as polymers used for spectacle lenses. Operation of the instrument is similar to that of its previous version, except that when the illuminator is activated, light emanates from the cap of the head to illuminate the surrounding tissue and is usually visible through the wall of the digestive tube (either directly, as in open surgery, or through the laparoscope or thoracoscope) and thus the location of the head with respect to the digestive tube is indicated.

Figure 4B:
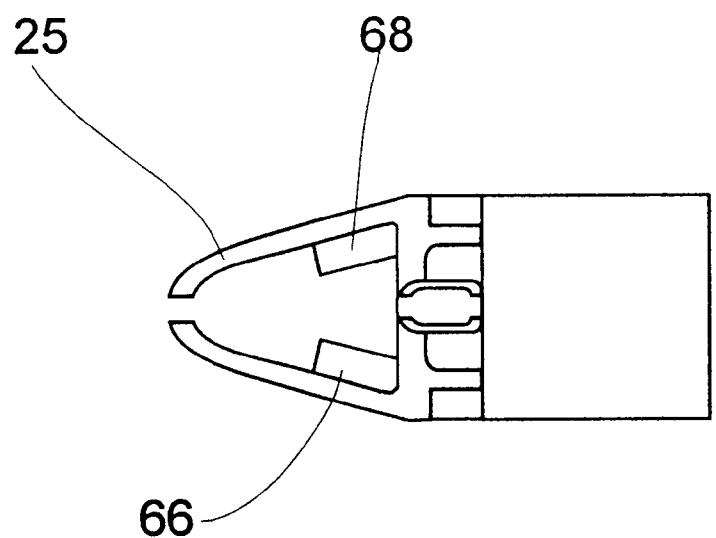
FIG. 4B is a longitudinal sectional view of the head of the stapler of the present invention with an alternative configuration for illumination.

It is noted that an optional passageway along the instrument is also shown in the French patent, where it, however, serves to supply air to a dilatation balloon at the tip of the head. The passageway according to the present invention must accommodate the optical fiber and may optionally serve for both the fiber and the air supply. According to an alternative embodiment, the optical fiber is replaced by a pair of wires, which are connected inside the head to a lamp and at the handle end—to a voltage source. In another alternative embodiment, shown in FIG. 4B, end cap 25 contains both a lamp 66 and a small battery 68; in this case there are no wires through the cable and thus no need for a passageway solely for the purpose of illumination; this alternative is most suitable for a disposable instrument. It is appreciated that the stapler shown in FIG. 4 is by way of example and that a flexible stapler of any construction can be modified to incorporate an internal illuminator according to the present invention.

Figure 5A:
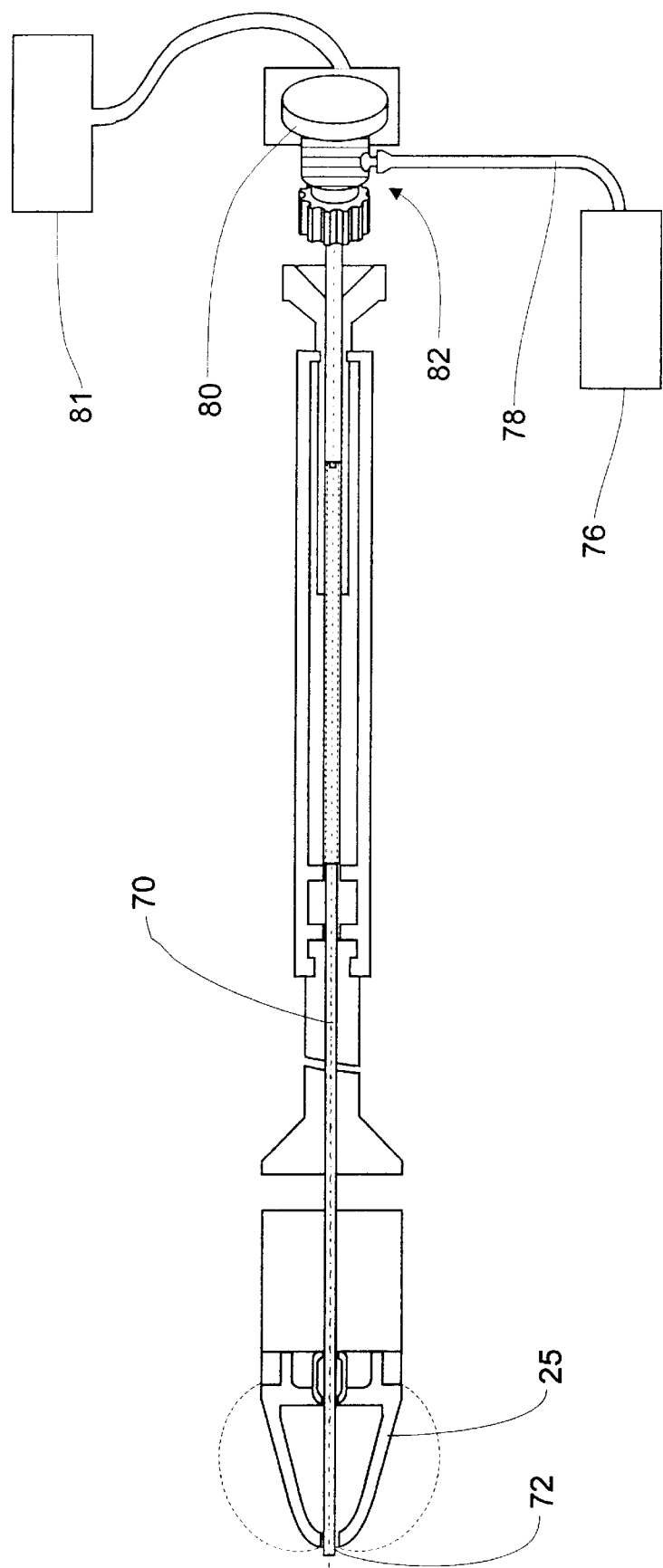
FIG. 5A is a side view of the stapler of the present invention, configured with an optical fiber viewing system.
Figure 5B:
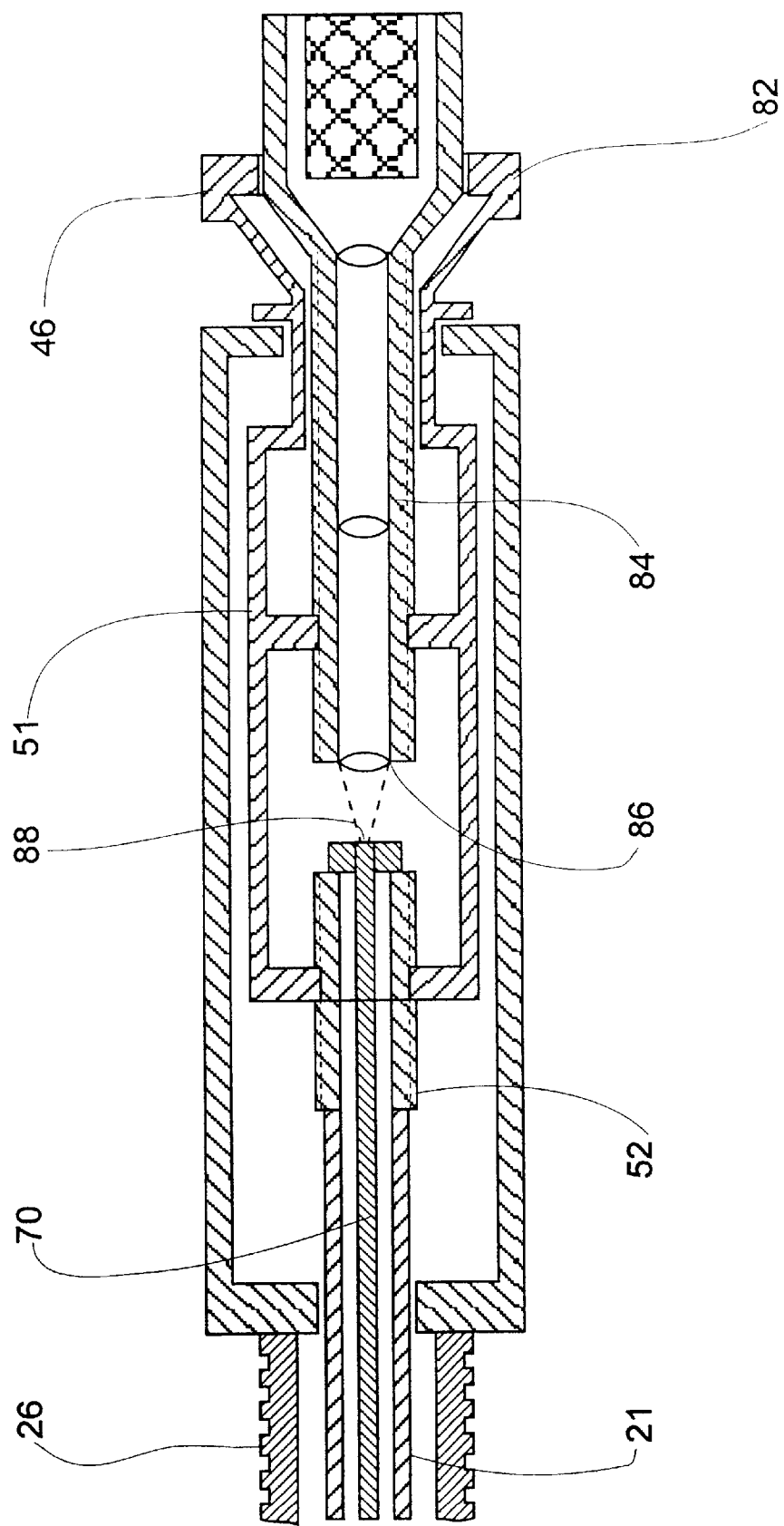
FIG. 5B is a longitudinal sectional view of the handle of a stapler of the present invention, showing a portion of the viewing system of FIG. 5A.

Another possible configuration is shown in FIG. 5A, which depicts a preferred embodiment of a flexible stapler with internal imaging facility. This is an augmented version of the configuration described hereabove in conjunction with Fio. 4A, whereby there is disposed through the passageway a coherent bundle of optical fibers 70. The end of the bundle of fibers protrudes through a hole in the end cap of the head, where an objective lens assembly 72, of any suitable design known in the art, serves to project an image of the surrounding inner wall of the intestines onto the near end of fiber bundle 70. Preferably a transparent balloon is stretched over end cap 25 (including the objective lens assembly) and inflated by air through the passageway; this aids in dilating the inner surface of the intestines and protects the surface of the lens. An illuminator 76 projects light into an illumination fiber 78, which runs through the passageway alongside fiber bundle 70 and whose other end also protrudes through the end cap, to illuminate the viewed area; it is appreciated, however, that other methods of illumination, as, for example, a separately inserted illumination fiber, may be employed. The other end of the fiber bundle, namely that which protrudes from the cable in the handle is terminated in a viewing assembly 82, which includes a video camera (not shown), for viewing the image on a video screen 81, and/or in an optical eyepiece 80, for direct viewing. The viewing assembly may be any of a number of commercially available models. In a disposable stapler the viewing assembly, including a lens 86 (FIG. 5B) for coupling it to the end of the fiber bundle, is reusable, whereas the fiber bundle and the optics in the head are disposable with the stapler. In this case the viewing assembly must be conveniently attachable to the end of the fiber bundle. One preferred way of doing this, depicted in the cross-sectional view of the handle in FIG. 5B, is to mount coupling lens 86 of viewing assembly 82 in a tube 84 that is externally threaded (like a screw) with a pitch identical to that of screw 52 at the end of cable 21; this tube is screwed into nut 51, which also engages screw 52 and is coaxially attached to the turning knob 46, so that the coupling lens is focused on an end 88 of fiber bundle 70 (which protrudes from the end of screw 52, which is hollow). Thus, when knob 46 is turned, to move cable 21 relative to body 26, viewing assembly 82 moves at the same rate, keeping it at a constant distance from end 88 of the fiber (which moves with the cable).

According to an alternative embodiment of the fiber-based imager, the fibers bundle terminates with an objective lens inside the head—similarly to the depiction in FIG. 4A. Clearly, in this case end cap 25 of the head should be transparent and made of optical-quality material, such as polymers used for spectacle lenses.

Figure 6:
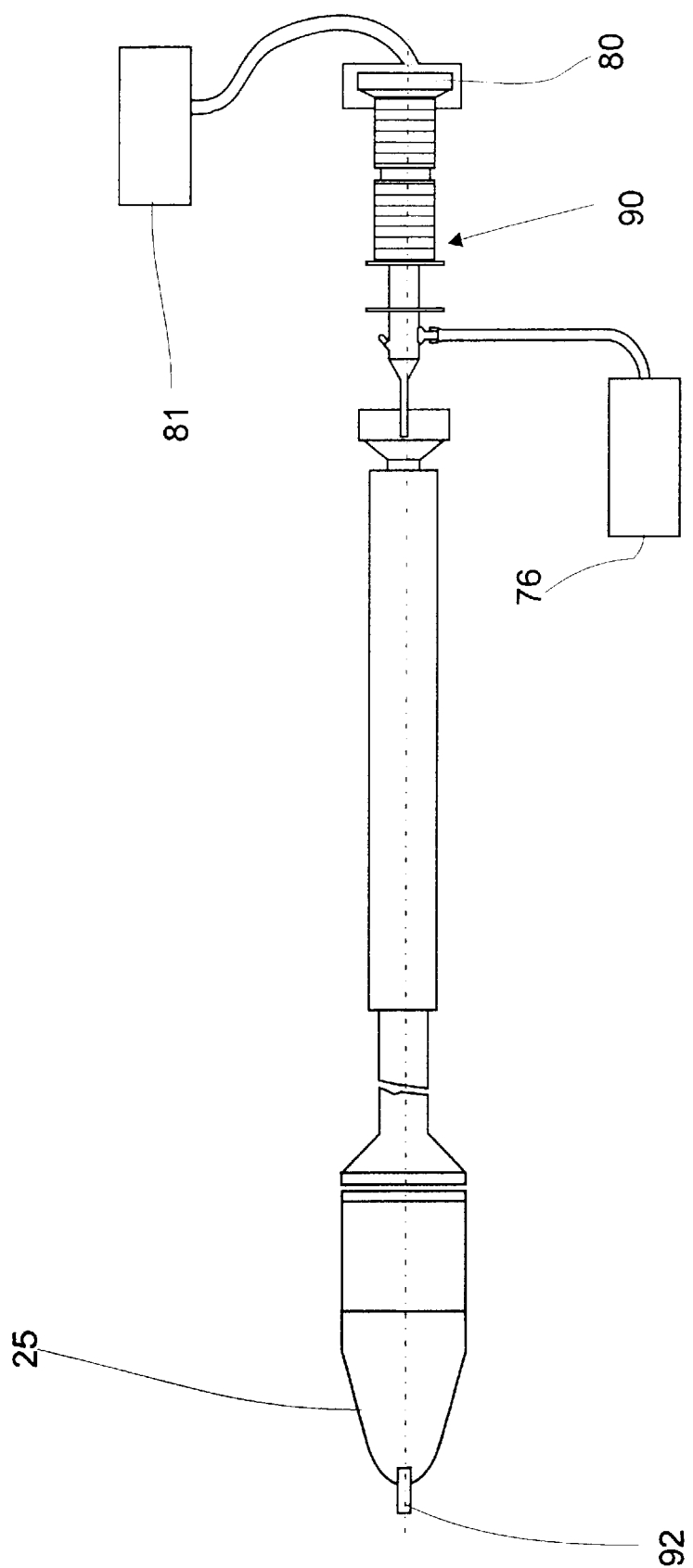
FIG. 6 is a longitudinal sectional view of the stapler of the present invention, configured with a commercial fibroscope.

Another alternative embodiment of a flexible stapler with an internal fiber-based imager is shown in FIG. 6: There is provided a passageway through the entire instrument of sufficient diameter to allow threading through it a suitable commercially available fibroscope 90. Such a fibroscope is available, for example, from the Ova-Med Corporation in Sunnyvale, California and usually includes an illuminator 76, an eyepiece 80 and a video screen 81. The tip 92 of the fibroscope can either protrude through a hole in end cap 25, as shown in the drawing, or be positioned inside a transparent cap, as in FIG. 4A. The advantage of this embodiment, over the previous one, is that it can easily be deployed or removed at will, thus saving its cost when not needed, especially when the stapler is disposable. It is appreciated that the same arrangement, that is a clear passageway through the entire instrument, including the cable and all its parts and possibly the end cap, can be utilized for a variety of thinly formed or catheter-like tools. Such tools may be specially made for the purpose or may be tools originally intended for other applications, such as laparoscopy, hysteroscopy, angioscopy, bronchospcopy, sinusoscopy, choledoscopy, etc.; they may include (beside a fibroscope or microendoscope), for example. an illuminator, a video camera, an ultrasonic probe, a suction device, a scraper, a surgical tool, an irrigator, a guide wire, etc.

Figure 7:
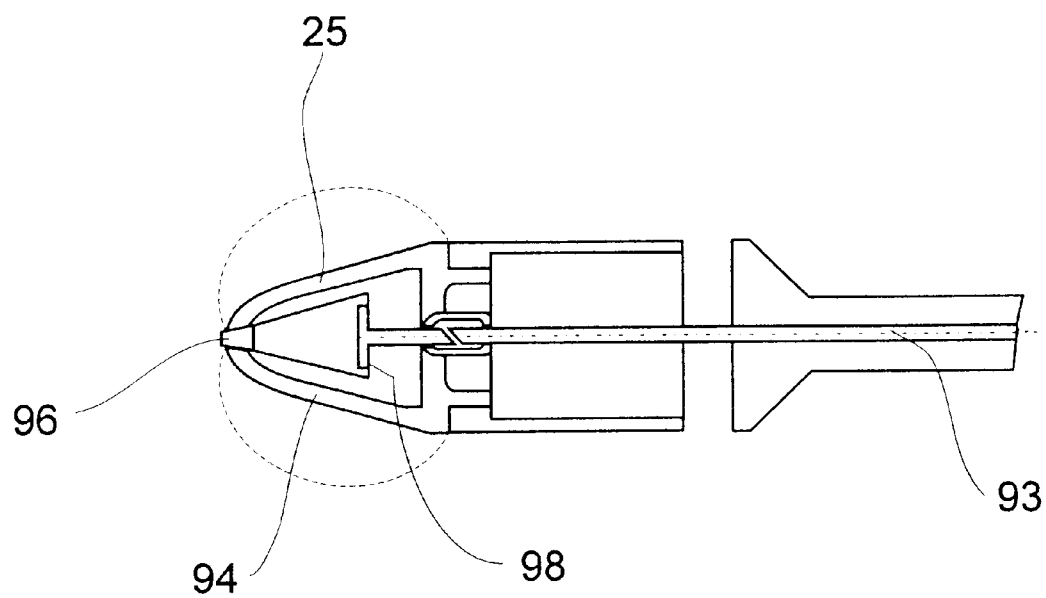
FIG. 7 is a longitudinal sectional view of the head and the cable's end segment of the stapler of the present invention, configured with a video camera.

Another configuration of a flexible stapler with an internal imaging facility is shown in FIG. 7. There is mounted inside cap 25 of the head a miniature video camera 94, consisting of an objective lens assembly 96 and an array of photoelectric devices 98, which is connected to an electronic drive circuit (not shown). The latter is connected to an electric cable 93 that runs through a passageway along the entire instrument and terminates at an electronic video assembly, which displays the image on a video screen. The miniature video camera and the external video assembly are commercially available. Illumination for the camera is, again, preferably provided by an illuminator as described hereabove, or by any other method. The lens 96 can alternatively be placed inside the cap, which is made transparent (similarly to FIG. 4A). If the stapler is to be disposable, the assembly of end cap and camera (which is too expensive to be disposable) is made to be easily attachable to the head.

Figure 8:
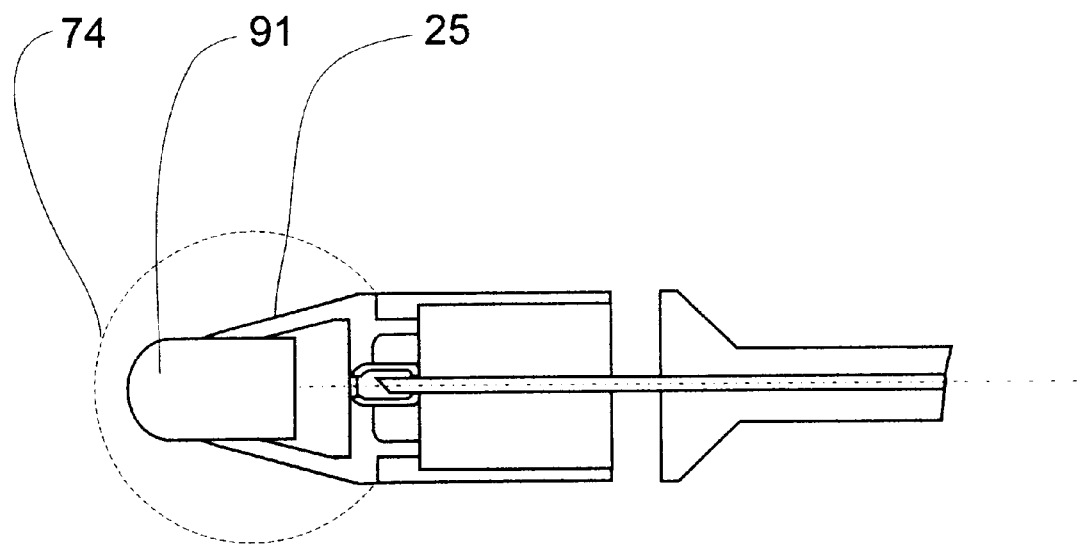
FIG. 8 is a longitudinal sectional view of the head and the cable's end segment of the stapler of the present invention, configured with an ultrasonic transducer.

Yet another configuration of the flexible stapler according to the present invention, which allows internal ultrasonic examination, is shown in FIG. 8. An ultrasonic transducer array 91 is mounted on end cap 25, preferably protruding therefrom, and connected by electric wiring through a passageway along the instrument to an external drive- and control console (not shown). An inflatable balloon 74 is stretched over the cap. Water, or another suitable fluid, is injected into the passageway, for example, by means of a syringe fitting into a hole in the center of knob 46 (FIG. 1B), and is made to inflate the balloon, through a hole in the end cap, until it makes good contact with the inner wall of the digestive tube. Alternatively, the fluid is supplied to the balloon through a catheter that is threaded through the passageway and protrudes through the hole in the cap. The ultrasonic array is then operated by means of the console in the usual manner.

Figure 9A:
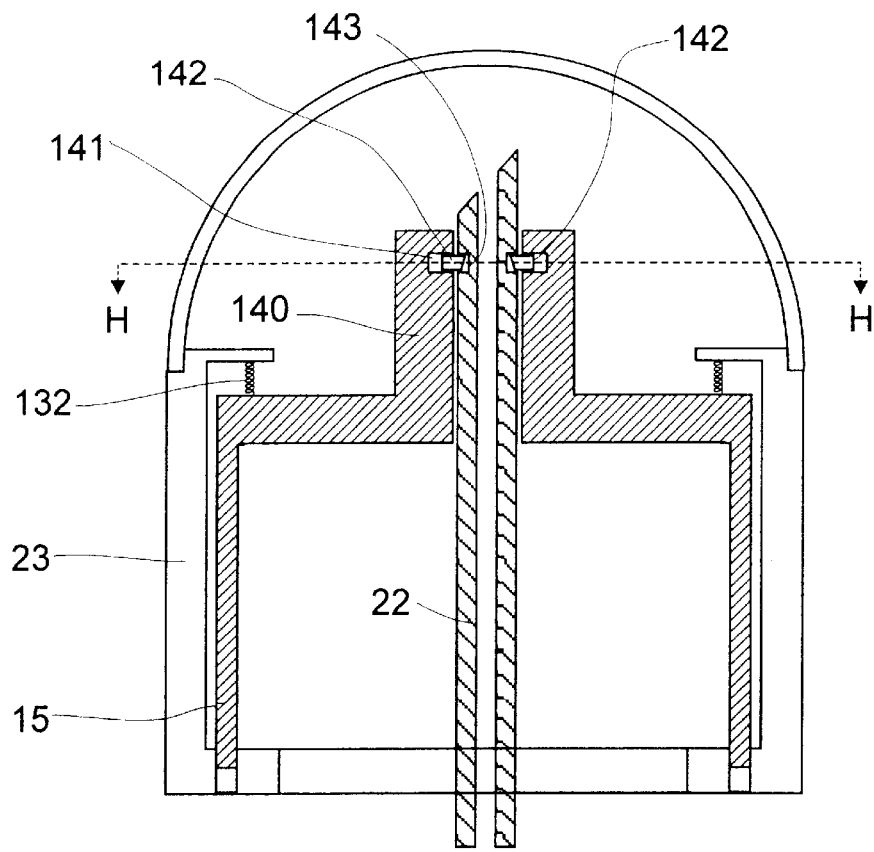
FIGS. 9A and 9B are a longitudinal sectional view and a cross sectional view, respectively, of the head and the cable's end segment of the stapler of the present invention, featuring a snap coupling.
Figure 9B:
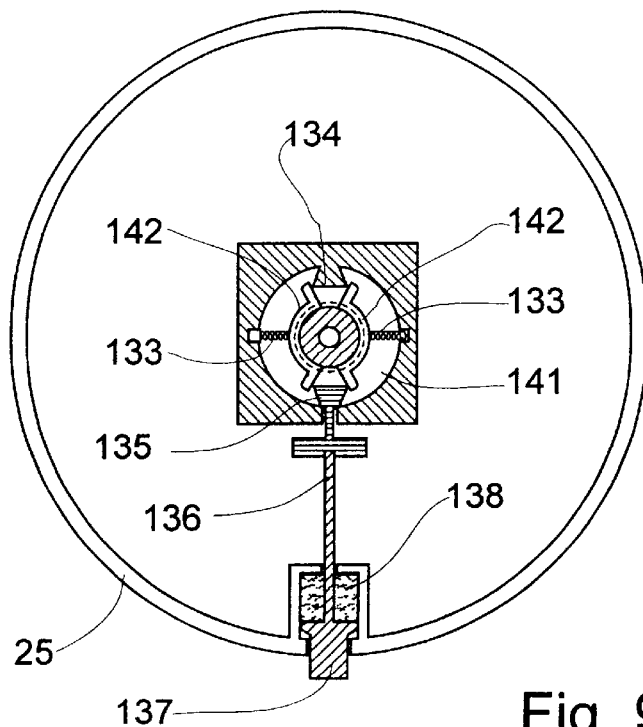

A novel configuration for attaching the head to the end of the flexible cable (alternative to the previously disclosed set screw arrangement) is a snap coupling, that is—an arrangement by which the head may be simply pushed onto the end of the cable until a flexible, or spring-loaded, member on the head engages a feature, such as a notch, on the cable and whereby the two parts thereafter remain interlocked until intentionally released. This feature is useful in certain procedures in that it enables easily attaching the head to the cable inside the patient's body, possibly inside the affected organ, and is particularly advantageous for closed surgery, as will be illustrated herebelow. There are many ways known in the art to 20 realize this configuration. One embodiment, presented here by way of example, is depicted in FIG. 9A, which shows a partial longitudinal-sectional view of the head, and FIG. 9B, which shows a cross-sectional view at the plane marked H—H in FIG. 9A. In this example, the head includes the hammer 15, which is connected to the shell 23 by tension spring 132. The end 22 of the cable is attachable to the hammer as follows: The top plate of the hammer 15 has around its center a ring-shaped protrusion 140, with a central hole that is a continuation of the hole through the top plate of the hammer and has therefore the identical size and shape. In the surface of that hole is a circular notch 141, which accomodates two arculate members 142. The arculate members 142, more clearly seen in FIG. 9B, are disposed symmetrically within notch 141 and each pressed inward by a compressive spring 133, the travel being stopped by two protrusions 134 and 135 within the notch. The end segment 22 of the cable has a notch 143 cut around it somewhat below its pointed tip, which notch accomodates any protruding portion of the arculate members 142. The inner surfaces of the arculate members 142 are bevelled so that when the members are at the stopped position, the arculate top and bottom edges of the bevelled inner surface are part of circles that are, respectively, somewhat smaller, and just greater, than the maximal diameter of the end segment of the cable between its tip and the notch 143 (which, preferably is somewhat smaller than the diameter of the rest of the end segment). Operation of this mechanism is as follows: The cable is initially detached from the head. When the end segment of the cable is pushed into the hole through the hammer, its pointed tip pushes on the bevelled inner surface of the arculate members, causing them to be pushed outward enough to allow the cable segment to slide in. When the notch in the cable segment reaches the arculate members, the latter snap back to their stopped state, engaging the notch and thus locking the cable segment to the hammer.

In order to unlock and release the cable from the head, there is provided, in the exemplary embodiment shown and as depicted in the cross-sectional view in FIG. 9B, a release mechanism as follows: The ends of arculate members 142 which touch the protrusions 134 and 135 are shaped to form funnels stradling the protrusions. One protrusion, 134, is fixed, while the other protrusion, 135, is movable and connected to a rod 136, which protrudes through the end cap 25 and ends with a button 137. A compressive spring 138 keeps the rod 136 and the protrusion 135 normally retracted. In order to unlock the snap mechanism, the button 137 is pushed, which cause the funnel-forming ends of arculate members 142 to be wedged by the two protrusions, thus pushing the arculate members apart—enough for the cable segment to be able to slide through. When the head is then pulled away from the cable, it is released. According to an alternative version of this embodiment, part of the rod 136 is made of soft iron and the rod is surrounded by an electromagnetic coil (disposed internally to the spring 138), so that when an electric current flows through the coil, it exerts a magnetic force on the rod in an inward direction. The coil is connected to an external switch and current source by a pair of conductors (not shown); each conductor consists of a pair of contact pads, one pad being on the end segment 22 of the cable and connected to a wire running through the cable and the other pad flexibly mounted on the hammer's protrusion 140 and connected by wire to the coil. To unlock the mechanism, the switch (located on an external console or on the handle) is simply closed. It is appreciated that even in the first version, the force needed on the button to effect unlocking action is small enough to be practically applicable inside the body under closed surgery.

Figure 10A:
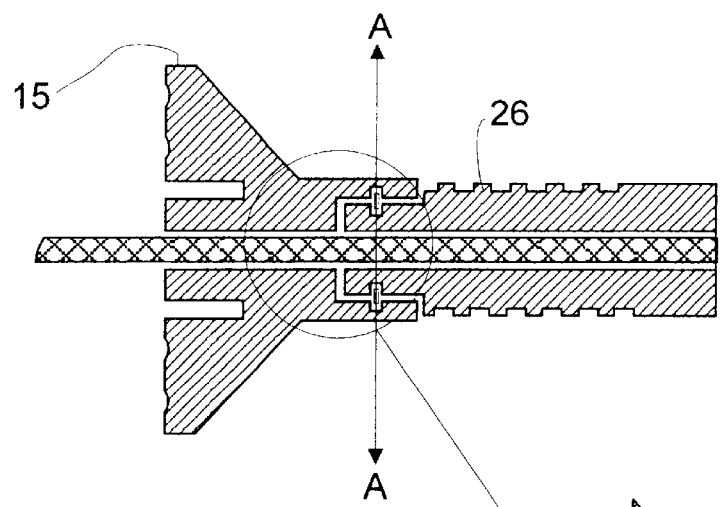
FIGS. 10A and 10C are a longitudinal sectional view and a cross sectional view, respectively, of the anvil and the end of the body of the stapler of the present invention, featuring a snap coupling.
Figure 10B:
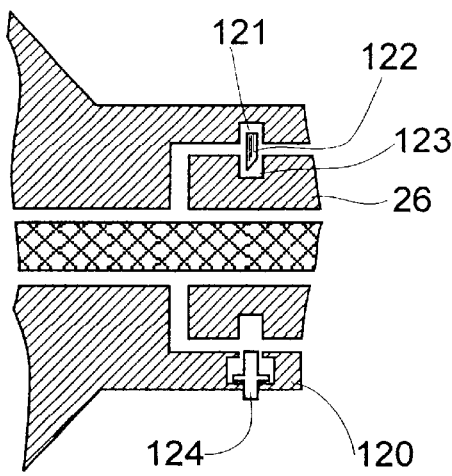
FIG. 10B is an enlarged detail of FIG. 10A.

A snap coupling configuration is also possible for the attachment of the anvil to the body. This feature as well is useful in certain procedures, in that it enables easily attaching the anvil to the body of the stapler inside the patient's body, possibly inside the affected organ, and is particularly advantageous for closed surgery, as will be illustrated herebelow. Again, many ways are known in the art for realizing this configuration. One possible embodiment, presented by way of example and illustrated in FIGS. 10A–10C, is similar to that described hereabove for attaching the head to the cable, though somewhat simpler, since there is no operative need to unlock inside the body.

The end of the body is attachable to the anvil as follows: As illustrated in FIG. 10A, which shows a longitudinal section, and FIG. 10B, which shows details of FIG. 10A, the bottom of the anvil 15 has around its center a ring-shaped protrusion 120, with a central hole that accomodates the cylindrically shaped end of the body 26. In the surface of that hole is a circular notch 121, which contains an open ring-shaped spring disc 122. The spring disc 122 is more clearly seen in FIG. 10C, showing a detailed cross sectional view of the protrusion area, at the line marked A—A in FIG. 10A. The inner surface of the spring disc 122 is bevelled so that when the disc is unflexed, its minimum inner diameter (near the disc's left surface) is somewhat smaller, and its maximum inner diameter (near the disc's right surface) just greater, than the diameter of the end segment of the body 26. The end segment of the body has a notch 123 cut around it, which notch accomodates any protruding portion of the spring disc 122. Operation of this mechanism is as follows: The body is initially detached from the anvil. When the end segment of the body is pushed into the hole at the anvil's protrusion 120, it pushes on the bevelled inner surface of the spring disk, causing it to be widened enough to allow the body segment to slide in. When the notch in the body segment reaches the spring disc, the latter snaps back to its unflexed state, engaging the notch and thus locking the body to the anvil.

Figure 10C:
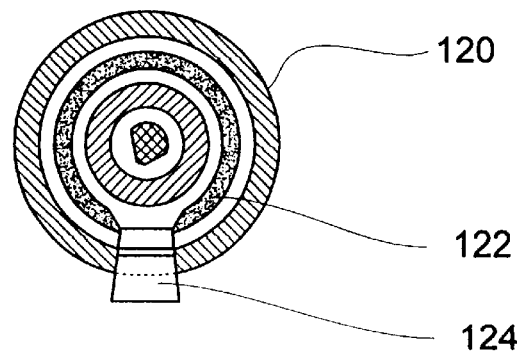

In order to unlock and release the body from the anvil, there is provided, in the embodiment shown and as depicted in the cross-sectional view in FIG. 10C, a wedge 124. The wedge is disposed opposite the opening in the spring disc 122 and is held within a hole through the ring 120, protruding therefrom. In order to unlock the snap mechanism, the wedge 124 is pushed, which causes it to press against the open ends of the spring disc and thus to widen it enough for the end of the body to be able to slide through. When the anvil is then pulled away from the body, it is released.

Figure 17A:
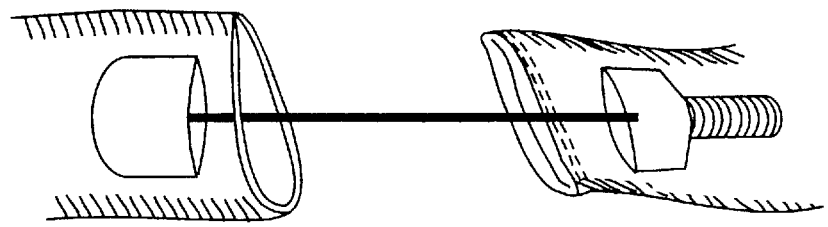
FIG. 17 is a sketch illustrating a method, according to the present invention, of closing butts organs to be joined by a flexible annular stapler.
Figure 17B:
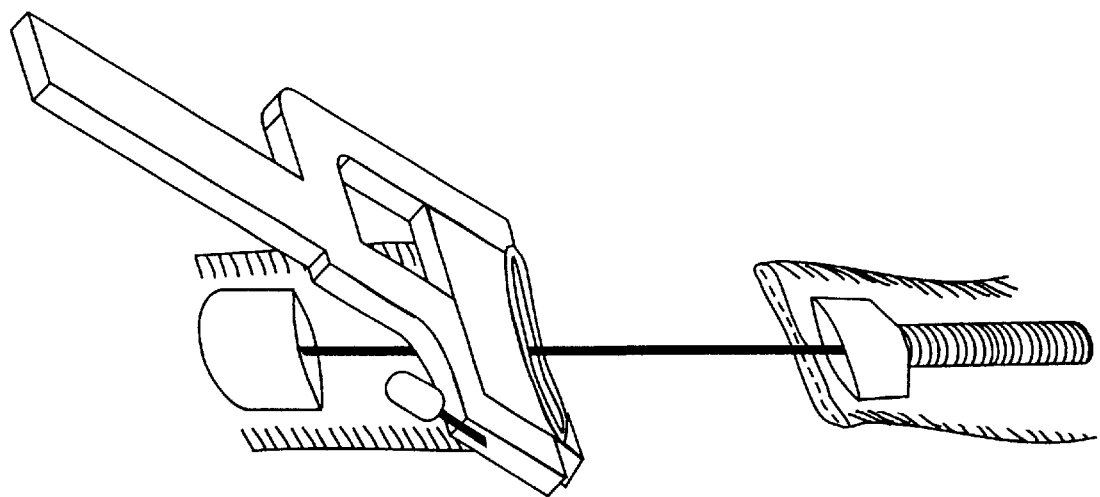

FIG. 17 illustrates schematically and by way of an example an improved method for generally preparing for, and performing, anastomosis of the digestive tube when utilizing a flexible stapler, such as disclosed herein or in the French patent. The present example concerns excision of a section of the colon. At the stage of the procedure shown, the affected part of the colon has been excised, leaving two open butts of the colon, and the stapler has been inserted so that its head 11 is just inside one butt and its anvil 18 is just inside the other butt, with flexible cable 21 connecting the two. The end of each butt is now pulled over the respective jaw and pressed together to form two lineal adjoining lips 110. The two lips are stapled together, by means of any linear stapler 112 used in the practice of open- or closed surgery, as the case may be. Such staplers are available, for example, from the U.S. Surgical Corporation. It is noted that the flexible cable, owing to its thinness, does not materially interfere with this stapling operation and allows the joining of the lips around itself. Subsequently the annular stapler is activated in the usual manner, whereby the two butt ends are pulled together, forming adjoining flanges, which are then stapled together annularly while their central discs are cut away. It is noted that the annular knife in the head of the stapler is generally hard enough to cut through staple pins left by the linear stapler. It is also noted that this method of preparing the butt ends for anastomosis is much easier and faster than the conventional method of hand sewing and that it is therefore particularly suitable for closed surgery. It is appreciated, however, that the method can also be advantageously used in open surgery.

It is noted that the improvements in flexible staplers and the methods utilizing them, described hereabove are applicable in any form of surgery of the digestive tube but are particularly advantageous in closed surgery. However, the very use of a flexible annular stapler in performing, anastomosis of the digestive tube under closed surgery in general is considered to be part of the present invention. The main advantage of such use is that the flexible stapler is insertable through the mouth or the anus or possibly also through a suitable trocar in the abdominal wall, to reach almost any location, thus eliminating the need for a wide incision through the wall—which is required for utilizing a conventional stapler. The other alternative—manual suturing or stapling—is much more difficult, particularly in closed surgery, and takes longer. Moreover, for some hard to reach locations such incisions are not possible and manual stitching is even more difficult, so that a flexible stapler is the only practical alternative. Further advantages of using a flexible stapler in general, or an improved one according to the present invention, in closed surgery of the digestive tube may be evident from the description of methods disclosed herebelow by way of examples.

Figures 11, 11A:
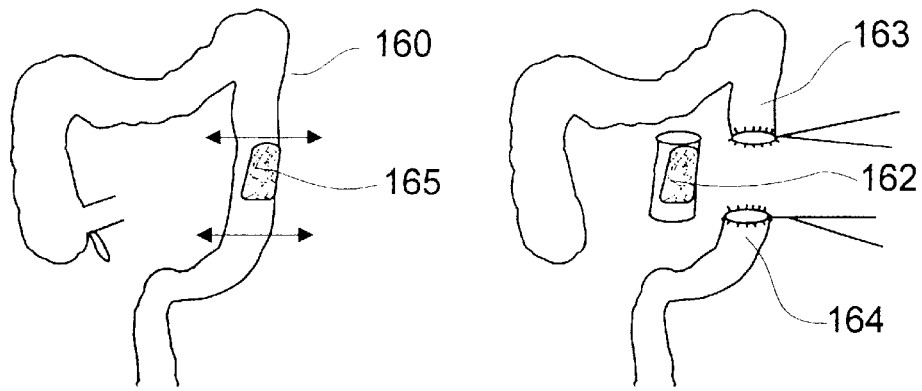
Figures 11B, 11C, 11D:
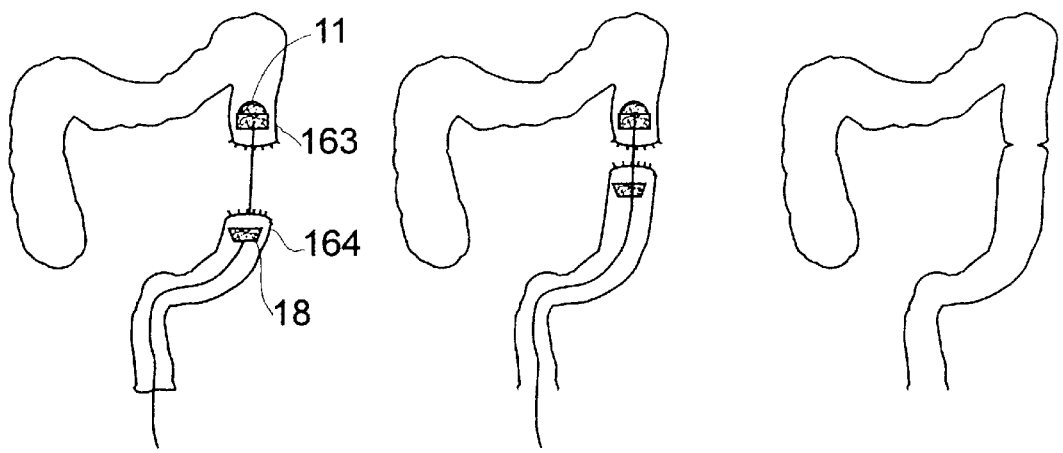
Figure 11E:
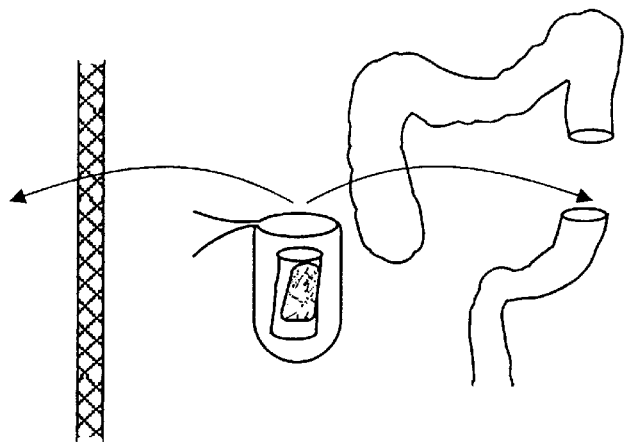

FIG. 11 illustrates schematically, by way of an example, the usage of a flexible stapler in a typical closed surgery of the digestive tube, which in this case aims at excision of a malignant section of the colon. First, the colon (160) is cut across below and above the malignancy (161) and the extirpated sement (162 dwg. 'A') is placed in a bag, which has been introduced, and is subsequently removed through an abdominal incision (as shown in 'E') or through the distal portion of the colon. At the next step, marked in the illustration as 'A', a thread is stitched like a purse-string around the end of each remaining segment (163 and 164). At the next step, the flexible stapler, with its head pulled close to its anvil, is pushed through the anus until the head protrudes from the lower segment; then the knob on the handle is turned until the head is sufficiently distant from the anvil, whereupon head 11 (dwg. 'B') is inserted into the upper segment (163), while keeping anvil 18 inside the lower segment (164). At the next step, which reaches the state illustrated in 'B', the thread at the end of each remaining segment is pulled. thus creating a flange of colon tissue closing on the anvil or the head. It is noted that the latter two steps can be advantageously replaced by the linear stapling method described hereabove. In the last step, illustrated in 'C', the knob is activated to pull the head and anvil together—to complete the anastomosis; subsequently the stapler is pulled back through the anus, leaving a well joined colon, as shown in 'D'.

It is noted that the last discussed example, as well as further examples to be discussed herebelow, concern end-to-end anastomosis. It is appreciated, though, that procedures can be similarly developed for end-to-side and side-to-side anastomoses.

FIG. 12 illustrate schematically an improved procedure for excising a malignant segment of a digestive tube, utilizing a flexible stapler; again, the example of a colon is used. First, the colon is sutured or, preferably, linearly stapled shut below the malignancy, then a cut is made across, just below the suture and the proximal, sutured butt (containing the malignancy) is bent away. Next the flexible stapler, with its head pulled close to its anvil, is pushed through the anus until the head protrudes from the (open) end of the distal segment; then the knob on the handle is turned until the head is sufficiently distant from the anvil. At this point the situation is as depicted in 'A'. Next, the end of the distal segment is sutured or, preferably, linearly stapled, to close on the anvil, and a lateral cut is made in the proximal segment of the colon above the malignancy, as depicted in 'B'. Then the head of the stapler is inserted into the upper colon through the lateral cut, as shown in 'C'. Next, the colon is sutured or. preferably, linearly stapled, to close on the head; it preferably is also sutured or linearly stapled shut just below the lateral cut; then the malignant segment is cut away from the sutured proximal butt, as shown in 'D'. Completing the lateral cut in that segment enables removing it from the cable, as in 'E'. Finally the handle is activated to pull the two butts together, as shown in 'F', and to then carry out stapling and cutting, as described hereabove. After pulling the stapler back out through the anus, the colon remains joined and clear, as shown in 'G'. It is noted that this method minimizes the time that the colon is open, thus minimizing possibility of soilage, which may be particularly bothersome under closed surgery, e.g. because of the more limited sponging ability. It is also noted that the method of linear stapling, described hereabove, is particularly convenient for the intermediate suturing- or stapling operations called for in the present procedure.

FIG. 13 illustrate schematically a further improved procedure for excising a malignant egment of a digestive tube, utilizing a flexible stapler; again, the example of a colon is used. This procedure utilizes a flexible stapler with an attachable head as described hereabove. It provides even cleaner preparation for anastomosis than does the previously described procedure and is therefore even more advantageous to closed surgery. According to this procedure, the colon is first sutured or stapled shut at two adjacent cross planes below the malignant segment, then cut across between the two planes, as shown in 'A', and the proximal butt is bent away. Next, the body of the stapler, with only the anvil attached, is inserted through the anus and pushed until the anvil reaches the sutured lower, distal butt; the progress of the anvil through the colon may be aided by threading a balloon, attached to a catheter, through the passageway along the instrument, disclosed hereabove, while the cable is kept maximally retracted, to just protrude from the anvil, and inflating the ballon. . Then the knob is turned to extend the flexible cable out of the anvil; its pointed end easily pierces this butt and protrudes therefrom, as illustrated in 'B'. Now the head is inserted through a suitable small incision in the abdominal wall, as, again, shown in 'B', and attached to the end of the cable; the snap-on feature described hereabove is particularly advantageous for such attachment. Subsequently, a lateral cut is made above the malignant segment and the situation is then as depicted in 'C', which is identical to that of FIG. 12B, so that the procedure continues as in the previously described procedure. It is again noted that the method of linear stapling, described hereabove, is particularly convenient for the intermediate suturing- or stapling operations.

Figure 14:
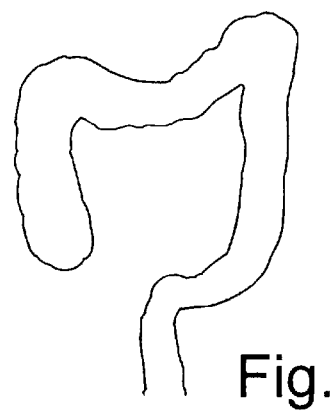
Figure 14A:
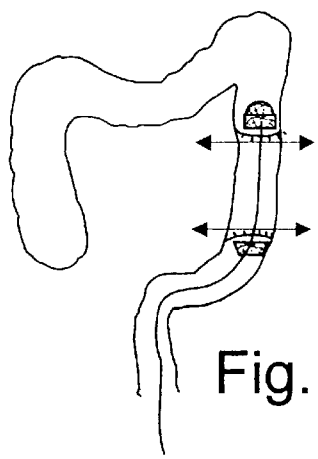
Figure 14B:
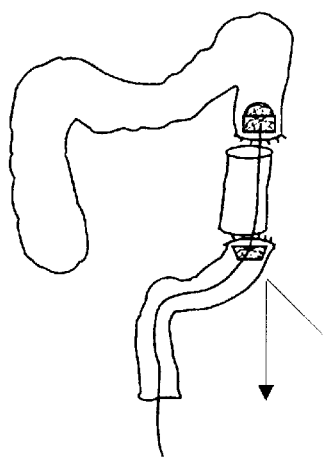
Figure 14C:
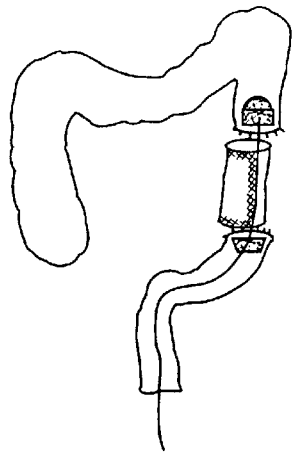
Figure 14D:
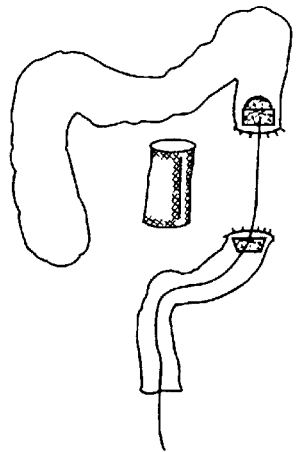
Figure 14C:
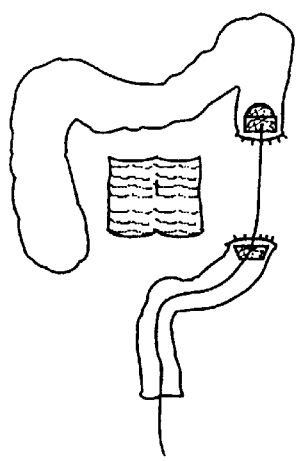
Figure 15A:
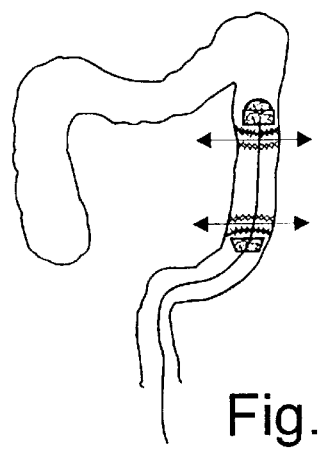
Figure 15B:
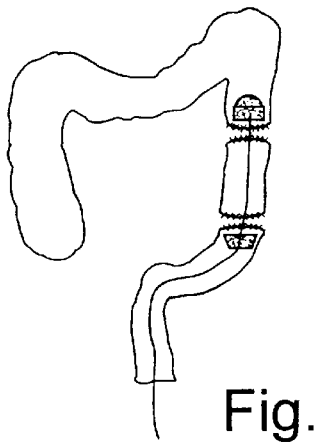
Figure 15C:
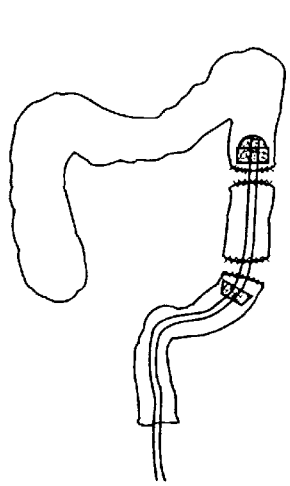
Figure 15D:
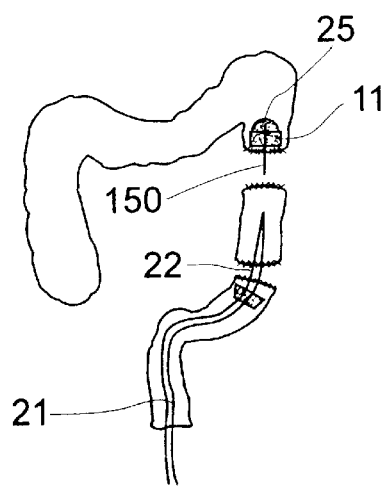
Figure 15E:
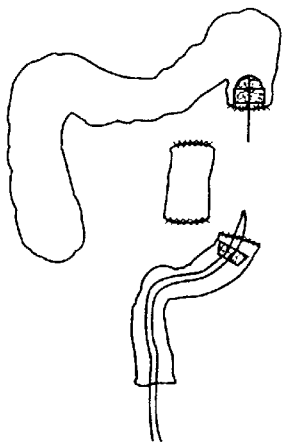
Figure 15F:
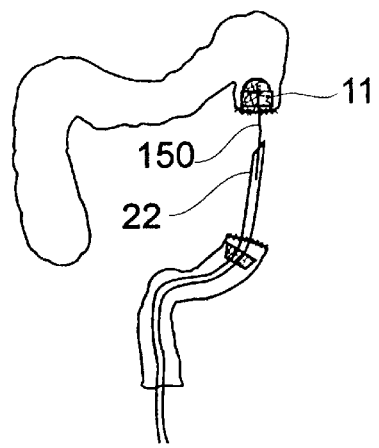
Figure 15G:
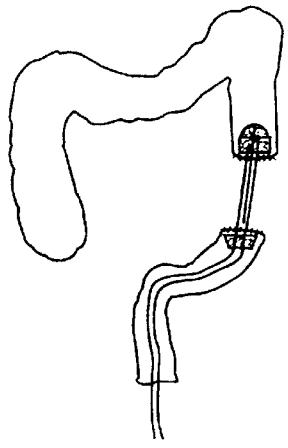
Figure 16A:
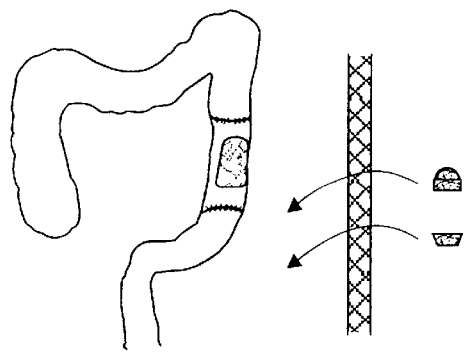
Figure 16B:
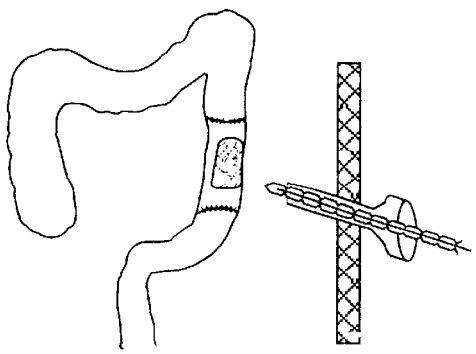
Figure 16C:
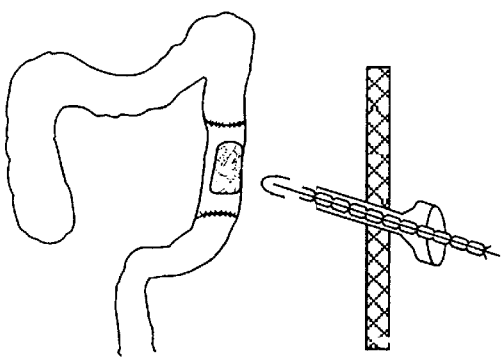
Figure 16D:
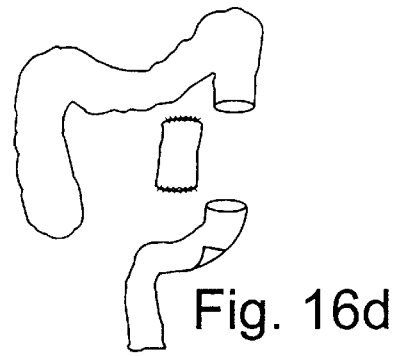
Figure 16E:
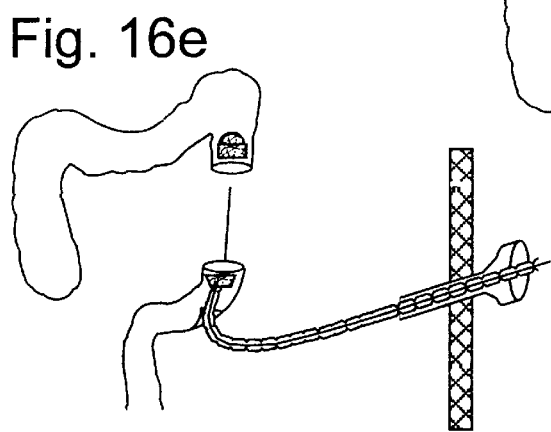
Figure 16F:
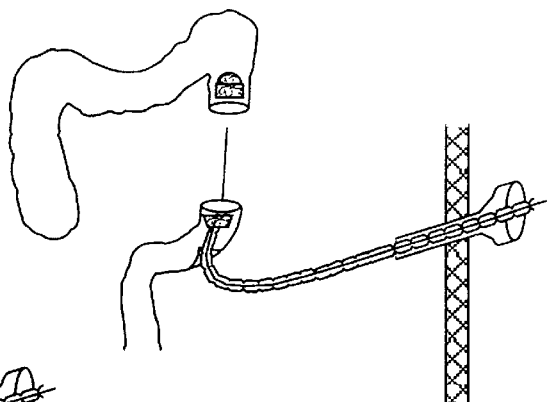
Figure 16G:
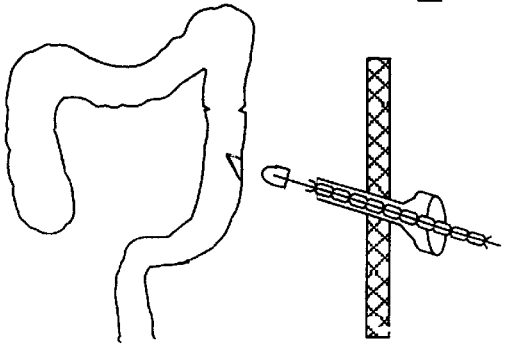
Figure 16H:
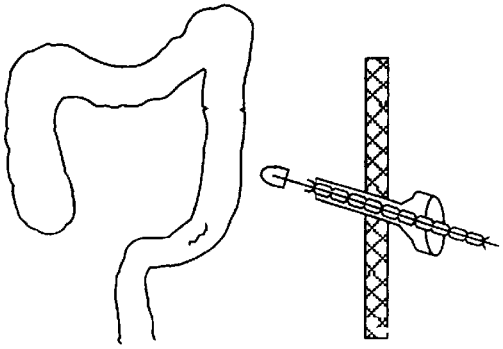

Another procedure utilizing a flexible stapler, which features even greater cleanliness and maximum simplicity, is illustrated schematically in FIG. 14—again by way of an example of excision in the colon. This procedure is suitable for cases where the affected segment is relatively clear, such as benign small tumors or inflammation. According to this procedure, the flexible stapler, with the head drawn close to the anvil, is first pushed through the anus until the head just reaches the affected segment; the knob is then turned to extend the head until it clears the affected segment; it is noted that the internal illumination attachment, disclosed in the present invention, is advantageous in locating the head with respect to the segment. Next, the colon is sutured or stapled just below the head and just above the anvil, to enclose them, and a cut is made across each end of the affected segment. next to the sutures, as depicted in 'A'; it is noted that here again the method of linear stapling is particularly convenient. Then, according to the preferred procedure, the affected segment, which is now loose but still enclosing the cable, is pushed to touch the cable, as shown in 'B'. Next, the segment is sutured or stapled across its ends as well as lengthwise, close to the cable, as depicted in 'C'; then it is cut lengthwise so as to free it from the cable, as shown in 'D'. An alternative procedure, which is shorter but somewhat less clean, is illustrated in 'Ca'; here the extirpated segment is simply cut lengthwise and folded away. In any case, the segment can be removed intact (e.g. in a bag) or after shredding. Subsequent operation is as described for previous procedures.

Yet another procedure utilizing a flexible stapler and suitable for cases where the affected segment is relatively clear is illustrated schematically in FIG. 15—again, by way of an example of excision in the colon. The stapler utilized in this procedure uses two features of the configurations described hereabove, namely (a) detachability and attachability of the head from, and to, the cable and (b) a clear passageway through the cable. In addition, head 11 is equipped with a short piece of guide wire 150, whose end is attached to the inside of end cap and which is normally disposed within the passageway in end segment 22 of cable 21. According to this procedure, which features ultimate cleanliness, the jaws are first inserted and positioned to straddle the segment to be excised in a manner similar to that described hereabove with respect to FIG. 14. Now, however, a pair of closely spaced sutures is made across the colon at each end of the affected segment, as shown in 'A'; it is again noted that the method of linear stapling is particularly convenient for carrying out these sutures. Then the colon is cut across between each pair of the sutures just made, as depicted in 'B'; it is noted that the three segments thus separated remain totally closed, thus preventing any soilage. Next, the cable is detached from the head and partially withdrawn, as shown in 'C'; then the bottom and middle segments are pulled away from the upper segment, to reach the situation depicted in 'D'. Now the middle, excised segment is removed, as shown in 'E'. Next, cable 21 is extended toward the head while end segment 22 is guided to slide around protruding guide wire 150, as illustrated in 'F'; it is then pushed through the suture at the end of the upper segment and into head 11, where it is again locked on to it, as shown in 'G'. Subsequent operation is then as described for previous procedures.

It is appreciated that the procedures described above are by way of examples only and that many variations and extensions are possible and that they can be applied also to organs other than the colon. These may be any of a number of hollow organs, including any part of the digestive tube (or alimentary tract) and organs external thereto, such as the gall bladder and the biliary tree, the urinary bladder and tree or the bronchial tree. The procedures may also be applied to joining two different ones of such organs, as well as to joining two different segments of the same organ.

Furthermore, neither of the parts to be joined need to be naturally tubular near the joint (like the cut end of the intestines), but may, for example, be a wall of the respective organ. What is common to all cases is that there is conceptually defined, for each of the two parts, a plane and an annular area thereon, the two annular areas being essentially congruent; during the joining operation, the two annular areas are brought together and conceptually combined into one annular area, over which the stapling and eventually the anastomosis take place. In the case that one of the parts is tubular at the joint, as in an end-to-end or end-to-side anastomosis, (in which case that part is always cut across) the defined plane is transverse and a short distance away from the plane of cutting; in the case that one of the parts presents an outer face of a wall at the joint, as in a side-to-end or side-to-side anastomosis, the plane is essentially at that face. Furthermore, in the case of a tubular part, there is an inherent opening through it at the defined plane and interior to the annular area (which opening is, in some procedures, not always initially accessible to the stapler, or, in some other procedures, may be intentionally closed off before the stapler reaches it), on the other hand, in the case of a part being joined at its wall, there is no such initial opening and, if required by a particular procedure (e.g. for insertion of part of the stapler thereto), a suitable opening has to be cut through the wall, interior to the annular area. Of course and as the raison d'etre, after the end of the procedure there remains in all cases a clear opening through both parts.

It is further appreciated that the stapler can also be inserted through openings other than the anus, including, in particular, the mouth and artificial openings through the body wall, such as practiced in closed surgery, and obviously also the wide opening of open surgery; clearly, insertion through such an artificial opening also requires a suitable lateral cut in the affected organ, for insertion of the stapler, or of ajaw, therein.

It is further appreciated that the pointed end of the cable can pierce the wall of an organ, or an artificially closed butt thereof, so as to protrude into, or out of, the organ.

Insertion of the stapler through the body wall may be called for during closed surgery in ases where the affected area is too far from a natural openinig, such as proximal portions of the small intestines, or where there are intervening obstructions or where none of the organs to be joined has a clear passageway to a natural opening. In such cases it may be possible to insert the stapler including the head and/or the anvil, through a sufficiently wide trocar. Such a wide trocar would, however, be generally considered inappropriate or disadvantageous. Fortunately, configurations with detachable head and anvil, particularly the snap-coupling configurations for attachment of the head and the anvil, described hereabove, enable alternative procedures, exemplified by the following, as illustrated in FIG. 16: Initially, the head is detached from the cable and the anvil is detached from the body. A small incision is made in the abdominal wall, through which the anvil and the head are pushed in (dwg. A). The body of the stapler, with the cable maximally retracted, is inserted through a trocar provided and installed for the purpose (dwg. B); a trocar having a nominal diameter of about 10 mm may be suitable. The anvil is then attached to the end of the stapler's body and the head is attached to the end of the cable (dwg. C); it is noted that the snap-coupling feature described hereabove is particularly advantageous for these operations. The affected segment of the colon is excised or otherwise prepared, using laparoscopic techniques. A lateral cut is then made in the colon (dwg D), and the two jaws at the end of the stapler are inserted therethrough and pushed until they reach their respective butt segments (dwg. E). The butt ends are then sutured over the two jaws (dwg F) and are pulled together and stapled, as described heretofore. Finally the stapler is pulled back (dwg. G) and out through the abdominal wall, together with the trocar (dwg 11). In some procedures it may be preferable to first insert the end of the body into the colon, through a small lateral cut, so that the body protrudes into the colon, then insert the anvil, through an open end of the segment or through another lateral cut, and attach it to the body, finally attaching also the head. It is appreciated that many variations of the procedures are possible—either analogous to procedures previously described or others.

What I claim is:

1. A flexible annular surgical stapler for stapling together two parts of hollow organs, the stapler comprising
    (a) an elongated flexible tubular body having two ends;
    (b) a handle attached to a first end of said body;
    (c) a flexible cable slidably disposed along the entire length inside said body having two ends, a first end being inside said handle;
    (d) a first jaw attached by snap-coupling to a second end of said cable and a second jaw attached to a second end of said body, wherein one of said first and second jaws includes a hammer and the other of first and second jaws includes an anvil; and
    (e) a hollow channel through said cable's entire length including said first jaw, wherein said channel and said first and second jaws are adapted to accommodate incorporation of at least one additional tool therethrough.

2. The stapler of claim 1, wherein said at least one additional tool is selected from the group consisting of an illuminator, a commercial fibroscope, a video camera, a catheter, an ultrasonic probe, a guide wire, a scraper, an irrigator and a surgical tool.

3. The stapler of claim 1, further comprising an ultrasonic transducer for ultrasonically probing tissue near said head.

4. The stapler of claim 3, wherein said ultrasonic transducer is attachable to said head.

5. The stapler of claim 1, further comprising an illuminator for illuminating tissue near said head.

6. The stapler of claim 5, wherein said head further includes an end cap.

7. The stapler of claim 6, wherein said end cap is translucent and said illuminator includes a light source disposed inside said end cap.

8. The stapler of claim 5, wherein said illuminator includes an optical fiber disposed inside and along said channel.

9. The stapler of claim 1, further comprising imaging optics for viewing tissue near said head, said imaging optics including a coherent fibers bundle disposed inside and along said channel.

10. The stapler of claim 9, wherein said fibers bundle has an open end protruding from said first end of said cable, the stapler further comprising a viewing assembly, attachable to said handle so as to be optically coupled to said open end of said bundle at a constant distance therefrom.

11. The stapler of claim 1, further comprising a video camera, for viewing tissue near said head.

12. The stapler of claim 11, wherein said video camera is attachable to said head.

13. The stapler of claim 1, wherein said channel is further operative to pass air or fluid to said head or to a balloon attached thereto.

14. A flexible annular surgical stapler for stapling together two parts of hollow organs, the stapler comprising
    (a) an elongated flexible tubular body having two ends;
    (b) a handle attached to a first end of said body;
    (c) a first jaw having an axial jaw hole therethrough and two faces, a first of said faces being attached to the second end of said body;
    (d) a flexible cable slidably disposed inside said body and through said jaw hole, said cable consisting of two portions, a first of said portions defining an end segment, at least part of which protrudes from the second of said faces of said first jaw, said end segment being stiffer than a second of said portions of said cable;
    (e) a second jaw, forming a head, being attachable to said end segment; said jaw hole having a non-circular cross-sectional shape and said end segment having a complementary cross-sectional shape such as to allow easy sliding of said end segment through said hole while keeping their mutual angular orientation about the axis of said hole fixed;
wherein one of said first and second jaws includes a hammer and the other of said first and second jaws includes an anvil; and
    (f) a hollow channel through said cable's entire length, including said end segment, wherein said channel is adapted to accommodate insertion of at least one additional tool therethrough.

15. The stapler of claim 14, wherein said at least one additional tool is selected from the group consisting of an illuminator, a commercial fibroscope, a video camera, a catheter, an ultrasonic probe, a guide wire, a scraper, an irrigator and a surgical tool.

16. The stapler of claim 14, further comprising an ultrasonic transducer for ultrasonically probing tissue near said head.

17. The stapler of claim 16, wherein said ultrasonic transducer is attachable to said head.

18. The stapler of claim 14, further comprising an illuminator for illuminating tissue near said head.

19. The stapler of claim 18, wherein said head further includes an end cap.

20. The stapler of claim 19, wherein said end cap is translucent and said illuminator includes a light source disposed inside said end cap.

21. The stapler of claim 18, wherein said illuminator includes an optical fiber disposed inside and along said channel.

22. The stapler of claim 14, further comprising imaging optics for viewing tissue near said head, said imaging optics including a coherent fibers bundle disposed inside and along said channel.

23. The stapler of claim 22, wherein said fibers bundle has an open end protruding from said first end of said cable, the stapler further comprising a viewing assembly, attachable to said handle so as to be optically coupled to said open end of said bundle at a constant distance therefrom.

24. The stapler of claim 14, further comprising a video camera, for viewing tissue near said head.

25. The stapler of claim 24, wherein said video camera is attachable to said head.

26. The stapler of claim 24, wherein said channel is further operative to pass air or fluid to said head or to a balloon attached thereto.

* * * * *